United States Patent [19]

Miller et al.

[11] 4,237,158
[45] Dec. 2, 1980

[54] 1-SUBSTITUTED ARALKYL IMIDAZOLES AND THEIR USE AS FUNGICIDES

[75] Inventors: George A. Miller, Maple Glen; Ronald P. Owen, Warminster, both of Pa.

[73] Assignee: Rohm and Haas Company, Philadelphia, Pa.

[21] Appl. No.: 741,442

[22] Filed: Nov. 12, 1976

Related U.S. Application Data

[63] Continuation-in-part of Ser. No. 642,041, Dec. 8, 1975, Pat. No. 4,105,762, which is a continuation-in-part of Ser. No. 547,291, Feb. 5, 1975, abandoned.

[51] Int. Cl.³ .................... C07D 233/60; A01N 9/22
[52] U.S. Cl. .................................424/273 R; 548/335; 548/341
[58] Field of Search ............... 260/309; 424/273; 548/335, 341

[56] References Cited

U.S. PATENT DOCUMENTS

| 3,321,366 | 5/1967 | Mussell et al. | 260/309 |
|---|---|---|---|
| 3,575,999 | 4/1971 | Godefroi et al. | 260/309 |
| 3,691,192 | 9/1972 | Büchel et al. | 260/309 |
| 3,711,487 | 1/1973 | Draber et al. | 260/309 |
| 3,769,422 | 10/1973 | Timmler et al. | 260/309 |
| 3,927,017 | 12/1975 | Heeres et al. | 260/309 |
| 3,991,201 | 11/1976 | Heeres et al. | 424/273 |
| 4,006,243 | 2/1977 | Strehlke et al. | 260/309 |
| 4,115,578 | 9/1978 | Miller et al. | 548/335 |
| 4,118,461 | 10/1978 | Miller et al. | 548/335 |

FOREIGN PATENT DOCUMENTS

| 1487326 | 5/1967 | France | 260/309 |
|---|---|---|---|
| 6751M | 4/1969 | France | |

OTHER PUBLICATIONS

Cannon et al., J. Org. Chem., 1957, vol. 22, pp. 1323–1326.
Lespagnol et al., J. Chim. Ther., 1966, vol. 66, pp. 292–300.

*Primary Examiner*—Henry R. Jiles
*Assistant Examiner*—Robert T. Bond

[57] ABSTRACT

This disclosure describes novel aralkyl imidazoles, their acid addition salts, their metal complex salts and processes for their preparation. These compounds possess biological activity and in particular are useful as systemic protectant/eradicant fungicidal agents for controlling plant diseases caused by fungi and as plant growth regulators. The metal complex salts of these compounds are particularly useful in their ability to reduce undesirable plant growth regulatory activity and phytotoxicity while retaining their ability for controlling plant diseases caused by fungi.

13 Claims, No Drawings

1-SUBSTITUTED ARALKYL IMIDAZOLES AND THEIR USE AS FUNGICIDES

SUMMARY OF THE INVENTION

This application is a continuation-in-part application of United States application Ser. No. 642,041, filed Dec. 8, 1975, now U.S. Pat. No. 4,105,762 which is a continuation-in-part application of United States application Ser. No. 547,291, filed Feb. 5, 1975, now abandoned.

The 1-substituted aralkyl imidazoles of this invention possess eradicant fungicidal properties which are unique in that they kill phytophathogenic fungi in infected plant tissues and therefore can be utilized after fungal infection has already occurred. The systemic properties of these compounds are equally unique in that the compounds will move both acropetally and basipetally in plant tissues. Furthermore, these compounds possess protectant properties against phytopathogenic fungi when applied to the plants prior to infection.

This invention is concerned with the preparation and use of 1-substituted aralkyl imidazoles of the formula:

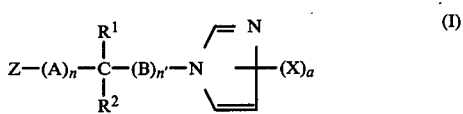

wherein Z is a ($C_6$–$C_{14}$) aryl or a substituted ($C_6$–$C_{14}$) aryl group; $R^1$ is a hydrogen atom, a ($C_1$–$C_{10}$) alkyl group; a ($C_2$–$C_{12}$) alkenyl group, a ($C_7$–$C_9$) aralkyl or substituted ($C_7$–$C_9$) aralkyl group; a phenyl or substituted phenyl group, a ($C_3$–$C_7$) cycloalkyl group, or a ($C_5$–$C_7$) cycloalkenyl group; $R^2$ is a ($C_1$–$C_{10}$) alkyl group, a ($C_2$–$C_{12}$) alkenyl group, a ($C_7$–$C_9$) aralkyl or substituted ($C_7$–$C_9$) aralkyl group; a phenyl or substituted phenyl group, a ($C_3$–$C_7$) cycloalkyl group, or a ($C_5$–$C_7$) cycloalkenyl group; $R^1$ and $R^2$ when taken together form a ($C_3$–$C_8$) cycloalkyl group; A and B are divalent ($C_1$–$C_5$) alkylene groups; X is a ($C_1$–$C_4$) alkyl group, a halogen atom or a nitro group; a is an integer from 0 to 3; n is the integer 0 or 1; n' is the integer 0 or 1; and the sum of n plus n' is equal to 1 or 2; or when Z is an unsubstituted phenyl group, $R^1$ is a hydrogen atom, A is methylene, and n' is 0, then $R^2$ is a ($C_4$–$C_{10}$) alkyl group, a ($C_2$–$C_{12}$) alkenyl group, a ($C_7$–$C_9$) aralkyl or substituted ($C_7$–$C_9$) aralkyl group, a phenyl or substituted phenyl group, a ($C_3$–$C_7$) cycloalkyl group or a ($C_5$–$C_7$) cycloalkenyl group.

A further embodiment of this invention is the metal salt complexes of the above 1-substituted aralkyl imidazoles having the formula:

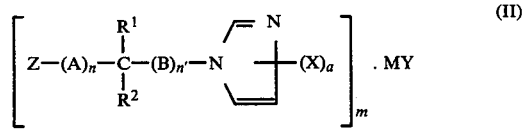

wherein Z, A, B, $R^1$, $R^2$, n, n', X and a are the same as above and M is a metal cation which can be selected from Groups IIA, IVA, VA, IB, IIB, VIB, VIIB and VIII of the Periodic Table. Y is a solubilizing anion counterion and m is 1–4.

In the above description of Z the term "aryl" refers to a phenyl, naphthyl, biphenyl, acenaphthenyl, indanyl, indolyl, pyridyl, pyrimidyl, pyrryl, furyl or thienyl group preferably a phenyl group which can be unsubstituted or substituted with up to three substituents preferably two substituents selected from the group consisting of ($C_1$–$C_4$) alkyl, methoxy, ethoxy, chloro, fluoro, bromo, iodo, nitro, amino, methylthio and trihalomethyl.

The terms "A" and "B" are divalent alkylene groups of from 1 to 5 carbon atoms which can be branched or straight chained.

The term "alkyl" in the description of $R^1$ and $R^2$ above refers to a straight or branched chain alkyl group of from 1 to 10 carbon atoms. The term "alkenyl" refers to a straight or branched chain alkenyl group of from 2 to 12 carbon atoms. The term "cycloalkyl" refers to a cycloalkyl group of from 3 to 7 carbon atoms and the term "cycloalkenyl" refers to a cycloalkenyl group of from 5 to 7 carbon atoms.

The term "aralkyl" refers to an aralkyl group of from 7 to 9 carbon atoms preferably benzyl or phenethyl which can be substituted with up to two substituents selected from the group consisting of ($C_1$–$C_4$) alkyl, methoxy, ethoxy, chloro, fluoro, bromo, iodo, nitro, amino, methylthio and trihalomethyl.

By the term substituted phenyl used in the definition of $R^1$ and $R^2$ is meant a phenyl group which can be substituted with up to two substituents selected from the group consisting of ($C_1$–$C_4$) alkyl, methoxy, ethoxy, chloro, fluoro, bromo, iodo, nitro, amino, methylthio and trihalomethyl.

The preferred compounds of this invention are those in which n' in Formulas I and II is one. The more preferred compounds of this invention are those in which n' is one and n is zero. The most preferred compounds of this invention are those in which n' is one, n is zero; $R^1$ is a hydrogen atom; a is zero; Z is a substituted phenyl group having up to three substituents selected from the group consisting of ($C_1$–$C_4$) alkyl, methoxy, ethoxy, chloro, fluoro, bromo, iodo, nitro, amino, methylthio and trihalomethyl, and $R^2$ is an alkyl group of from 4 to 10 carbon atoms, an alkenyl group of from 2 to 12 carbon atoms, an aralkyl group of from 7 to 9 carbon atoms which can be substituted with up to two substituents selected from the group consisting of ($C_1$–$C_4$) alkyl, methoxy, ethoxy, chloro, fluoro, bromo, iodo, nitro, amino, methylthio and trihalomethyl; a phenyl group which can be substituted with up to two substituents selected from the group consisting of ($C_1$–$C_4$) alkyl, methoxy, ethoxy, chloro, fluoro, bromo, iodo, nitro, amino, methylthio and trihalomethyl; a cycloalkyl group of from 3 to 7 carbon atoms or a cycloalkenyl group of from 5 to 7 carbon atoms.

A preferred embodiment of this invention is a chemical compound selected from the group consisting of an imidazole derivative having the formula

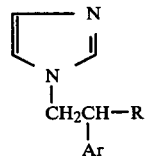

and the active acid addition salts thereof wherein Ar is a member selected from the group consisting of phenyl, mono-, di- and trihalophenyl, methylphenyl, ethylphenyl, methoxyphenyl, ethoxyphenyl, nitrophenyl and trihalomethylphenyl, and R is a member selected from the group consisting of ($C_1$–$C_{10}$) alkyl, cycloalkyl, alkenyl, cycloalkenyl and aralkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl, provided that when Ar is unsubstituted phenyl then R is ($C_4$–$C_{10}$) alkyl, cycloalkyl, alkenyl, cycloalkenyl and arylalkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl.

Typical compounds encompassed by this invention include:

1-[β-(2,4-dichlorophenyl)hexyl]imidazole
1-[β-(2-chlorophenyl)hexyl]imidazole
1-[β-(4-bromophenyl)hexyl]imidazole
1-[β-(3-iodophenyl)hexyl]imidazole
1-[β-(2,6-dichlorophenyl)decyl]imidazole
1-[β-(2,4-dichlorophenyl)β-(p-chlorophenyl)ethyl]imidazole
1-[α-(2,4-dichlorobenzyl)pentyl]imidazole
1-[β-(2,4-dichlorobenzyl)hexyl]imidazole
1-[β-(2-methyl-4'-chlorophenyl)heptyl]imidazole
1-[β-(2,4-dichlorophenethyl)hexyl]imidazole
1-[β-(2,4-dichlorophenyl)nonyl]imidazole
1-[β-(2,4-dimethylthiophenyl)hexyl]imidazole
1-[β-(4-(nitrophenyl)hexyl]imidazole
1-[β-(3,4-dichlorophenyl)hexyl]imidazole
1-[β-(4-tolyl)hexyl]imidazole
1-[β-(4-anisyl)hexyl]imidazole
1-[β-(2,4-dichlorophenyl)-β-cyclopropyl ethyl]imidazole
1-[β-(2,4-dichlorophenyl)-β-cyclopentyl ethyl]imidazole
1-[β-(2,4-dichlorophenyl)-β-cycloheptyl ethyl]imidazole
1-[β,β-trimethylene-β-(2',4'-dichlorophenyl)ethyl]imidazole
1-[β,β-pentamethylene-β-(2',3'-dibromophenyl)ethyl]imidazole
1-[β,β-heptamethylene-β-(3',5'-difluorophenyl)ethyl]imidazole The compounds of this invention can be prepared by standard methods of synthesis. Typical methods of preparation which can be utilized in the preparation of these compounds include the following general syntheses, the temperatures given unless indicated otherwise are in degrees centigrade.

1-(β-substituted alkyl) imidazole

When the proper acetate derivative (III) is reacted with sodium hydride in tetrahydrofuran or glyme it forms the corresponding sodio salt (IV). The reaction of (IV) with an organic halide affords the ester (V).

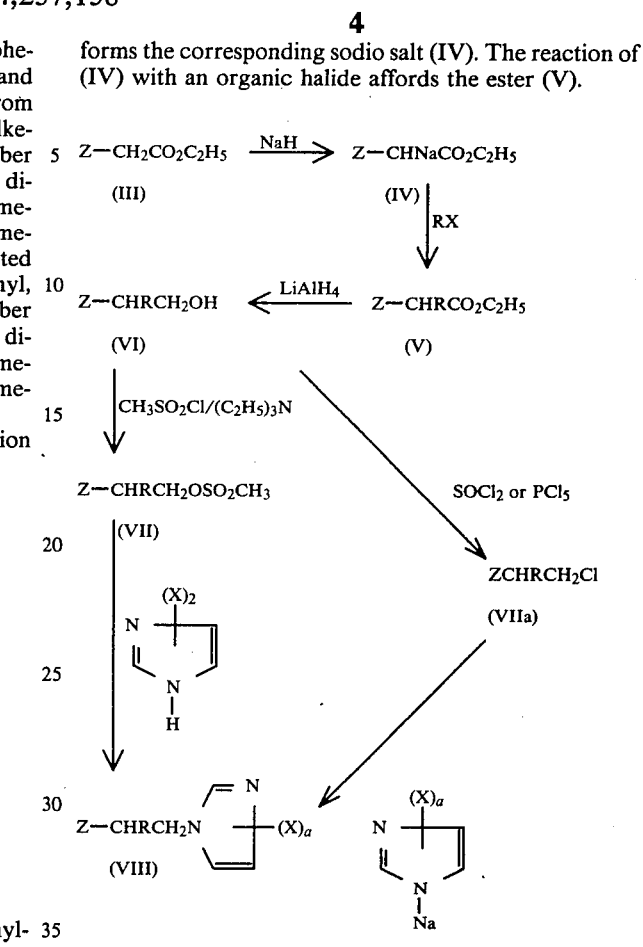

These esters (V) are converted to the corresponding carbinol derivatives (VI) by a reduction with reagents such as lithium aluminum hydride (LiAlH$_4$) in ether or bis(2-methoxyethoxy) aluminum hydride in benzene. The subsequent treatment of (VI) with methane sulfonyl chloride in the presence of triethyl amine in an aromatic hydrocarbon solvent such as benzene or toluene provides the sulfonate (VII). Treatment of (VI) with thionyl chloride or phosphorus pentachloride in an aromatic hydrocarbon such as benzene or toluene provides the chloride (VIIa). The reaction of (VII) with excess of an imidazole or (VIIa) with the sodium salt of an imidazole either neat or in the presence of such solvents as benzene, glyme, N,N-dimethylformamide, etc., gives the alkylated imidazole products (VIII).

1-(α-substituted alkyl) imidazole

The 1-(α-substituted alkyl) imidazoles are synthesized by a different route.

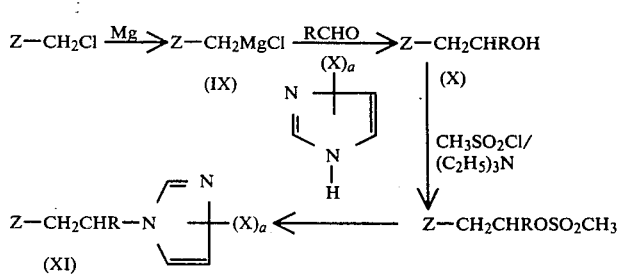

The Grignard reagent (IX) is formed from the reaction of magnesium metal with the appropriate organic chloride in ether. This reagent (IX) subsequently reacted with the desired aldehyde to provide the carbinol derivative (X). The formation of the sulfonate or chloride followed by its reaction with an imidazole or its sodio salt is carried out by the previously described route to give the product (XI).

Methylene Chain Extension-Malonate Route

A malonate synthesis is utilized to provide the starting materials for some other closely related analogues where the methylene chain is extended.

alkylated imidazole product (XVII) is then formed by the usual route.

Methylene Chain Extension

The methylene chain can be extended from the methane sulfonate (VII) via the preparation of the nitrile (XVIII).

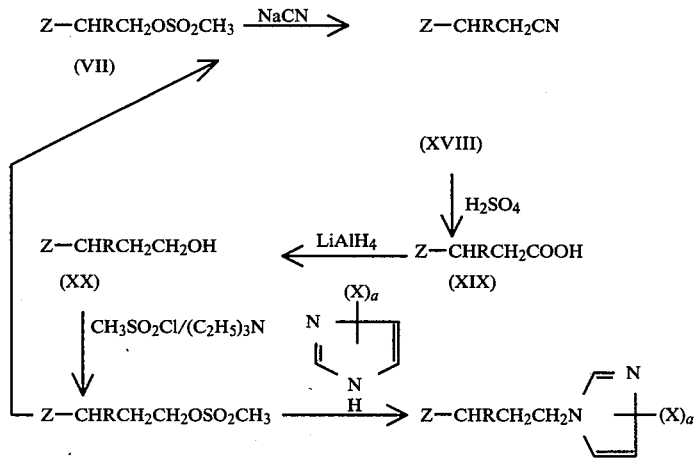

This sulfonate (VII) in DMF is treated with sodium cyanide in DMF to give the nitrile derivative (XVIII). The hydrolysis of (XVIII) in boiling 50% sulfuric acid provides the acid (XIX) which is subsequently reduced with LiAlH$_4$ to provide the alcohol (XX). The imidazole derivative is then formed via the sulfonate in the

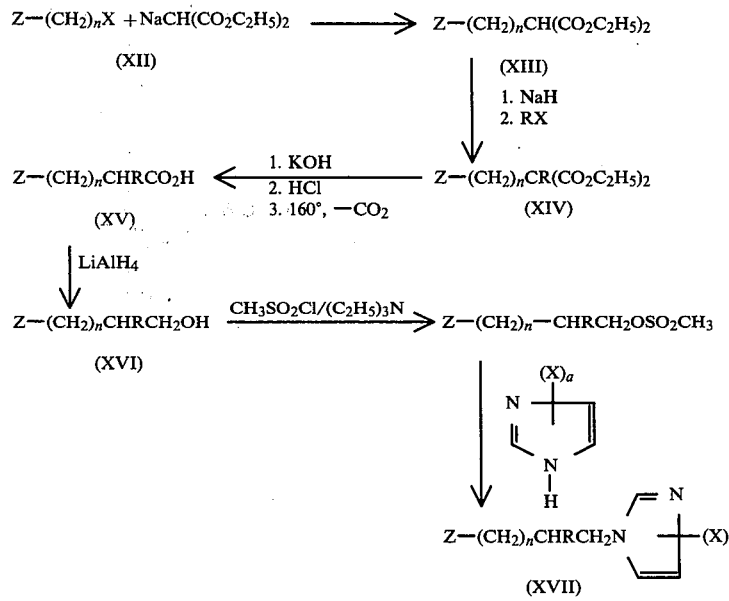

The reaction of an alkyl halide (XII) with sodio ethyl malonate in a solvent such as THF or glyme gives the substituted malonate (XIII). A further reaction of (XIII) with first sodium hydride in THF followed by the addition of the appropriate organic halide affords the disubstituted ester (XIV). A basic hydrolysis of (XIV) and a subsequent acidification and decarboxylation gives the mono acid (XV). The reduction of (XV) with LiAlH$_4$ gives the corresponding carbinol derivative (XVI). The usual way or the sulfonate can be recycled through the process for further chain extension.

Phenyl Analogues

The synthesis of the phenyl substituted analogue involves a Darzen's reaction. A substituted benzophenone is reacted with ethyl chloroacetate in the presence of sodium hydride to give the glycidic ester (XXI).

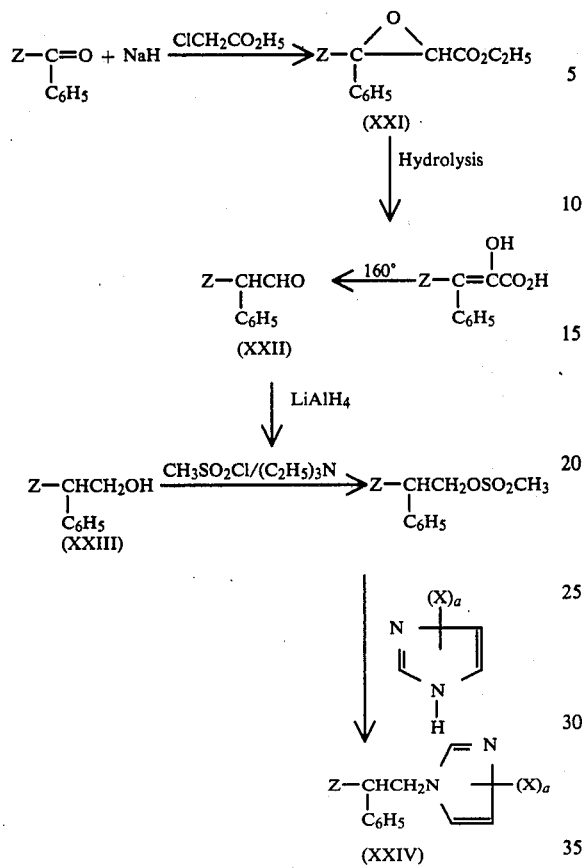

A hydrolysis and a subsequent decarboxylation of (XXI) gives the diaryl acetaldehyde (XXII). This aldehyde (XXII) is reduced to the corresponding alcohol (XXIII) by LiAlH$_4$, and it is then converted to the alkylated imidazole product (XXIV) by the usual route.

α,β-Disubstituted alkylimidazole

The Friedel-Craft acylation of a substituted aromatic hydrocarbon with an acyl halide in the presence of aluminum chloride either neat or with a halogenated hydrocarbon provides the desired product (XXV).

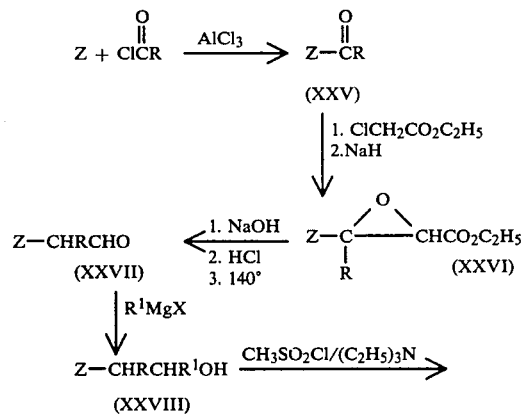

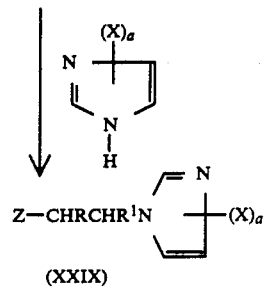

Treatment of (XXV) with an excess of ethyl chloroacetate and sodium hydride gives the glycidic ester (XXVI) which upon saponification with base and hydrolysis with hot mineral acid followed by decarboxylation gives the aldehyde (XXVII). A Grignard Reaction with an alkyl or aryl magnesium halide yields the alcohol (XXVIII). The formation of the sulfonate followed by its reaction with an imidazole as previously described gives the product XXIX.

β,β-disubstituted alkyl imidazole

When the appropriate sodio alkyl acetate derivative (XXX) prepared as previously described is reacted at elevated temperatures in a solvent such as ether, tetrahydrofuran or dimethylformamide with an iodoalkane the desired trisubstituted acetate (XXXI) is obtained.

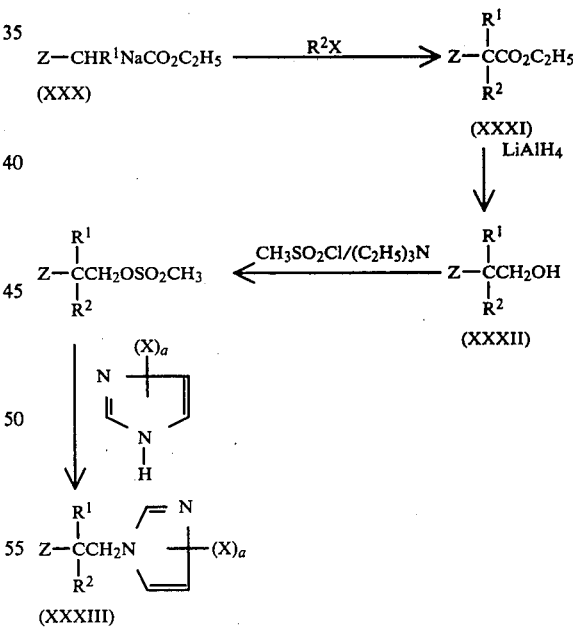

Reduction of (XXXI) with LiAlH$_4$ in anhydrous ether gives the alcohol (XXXII). Formation of the sulfonate followed by the imidazole reaction as previously described gives the desired product (XXXIII).

Alternate Routes to Phenyl Analogues

The reduction of a substituted phenylacetic acid (XXXIV) with LiAlH$_4$ in tetrahydrofuran gives the alcohol (XXXV).

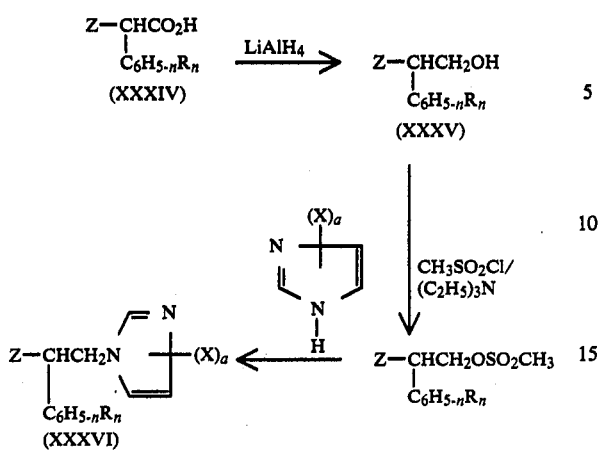

Formation of the sulfonate by reaction with an imidazole gives the desired product (XXXVI).

1-(β-substituted diarylalkyl) imidazole

The reaction of chloroacetaldehyde diethylacetal with a substituted aromatic hydrocarbon in the presence of sulfuric acid at room temperature gives the substituted arylethylchloride (XXXVII). The reaction of (XXXVII) with the sodium salt of an imidazole as previously described affords the product (XXXVIII).

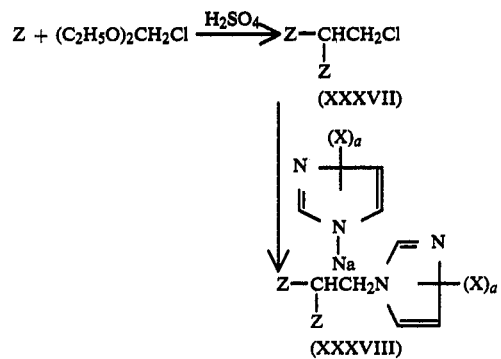

1-[ε-(substituted aryl) hexyl]imidazole

When a substituted aromatic hydrocarbon is treated with 1,2-epoxyhexane in the presence of aluminum chloride the rearranged hexanol (XXXIX) is obtained.

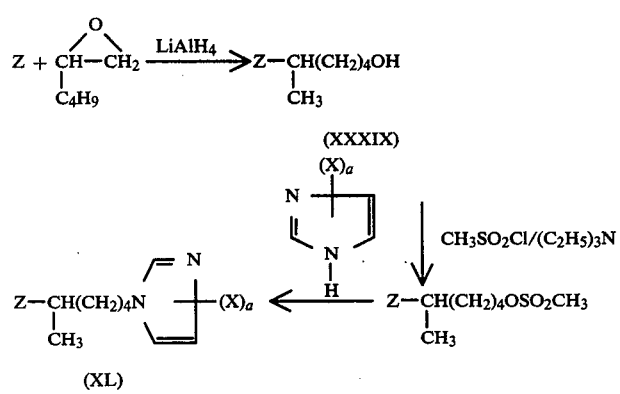

Formation of the methane sulfonate followed by the reaction with an imidazole gives the product (XL).

When a benzene substituted with electron donating groups is treated with 1,2-epoxyhexane in the presence of stannic chloride the hexanol (XLI) is obtained.

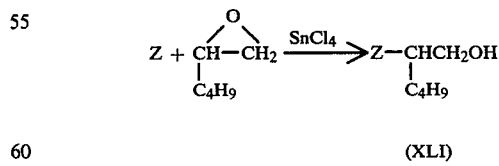

The imidazole derivative is formed via the above route from the methane sulfonate.

1-[β-(alkylthio or alkylsulfonyl substituted phenyl) alkyl]imidazoles

The alkylthio and alkylsulfonyl derivatives are prepared from the aldehyde (XLII).

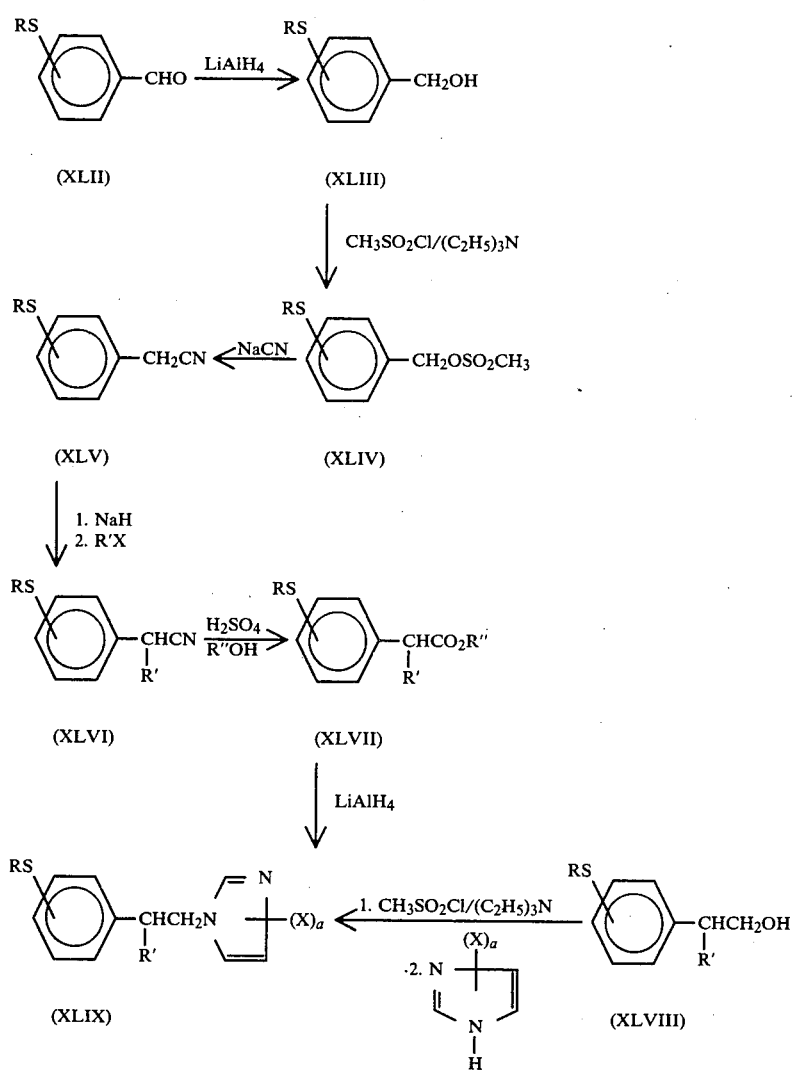

The aldehyde (XLII) is reduced to the alcohol (XLIII) with LiAlH$_4$. The alcohol (XLIII) is reacted with methane sulfonyl chloride in the presence of triethylamine to form the sulfonate (XLIV). Treatment of the methane sulfonate (XLIV) with sodium cyanide gives the benzyl nitrile derivative (XLV). Alkylation of the nitrile (XLV) via NaH metallation followed by treatment with alkylhalide gives the α-alkyl benzyl nitrile derivative (XLVI). Hydrolysis of the nitrile (XLVI) with sulfuric acid in an alcoholic solvent gives the α-alkyl phenylacetic acid ester (XLVII) which upon reduction with LiAlH$_4$ gives the phenethyl alcohol (XLVIII). The imidazole product is formed via the methane sulfonate as shown above. When the imidazole (XLIX) is oxidize with hydrogen peroxide in acetic acid the alkylsulfonyl (L) is formed.

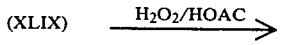

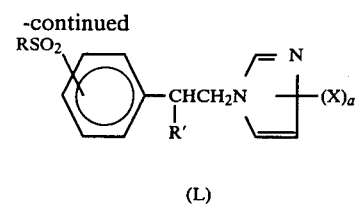

1-[β-(nitro substituted phenyl) alkyl]imidazole

The nitro substituted phenyl derivatives (LII) are formed by nitration of the unsubstituted or substituted analogs (LI).

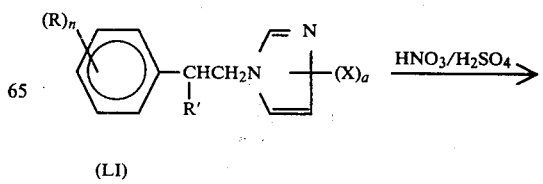

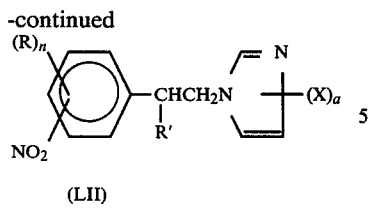

(LII)

1-[β-(amino substituted phenyl) alkyl]imidazole

The amino substituted phenyl derivatives (LIII) are formed by reduction of the nitro substituted phenyl derivative.

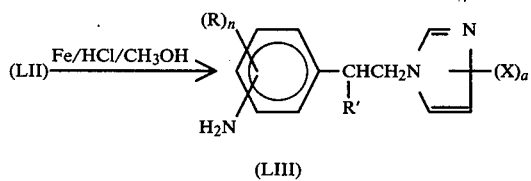

Substituted imidazole derivatives

The analogs in which the imidazole rings itself is substituted (LV) are prepared by reacting the appropriate methane sulfonate (LIV) with either an excess of the substituted imidazole or the sodium salt of the imidazole.

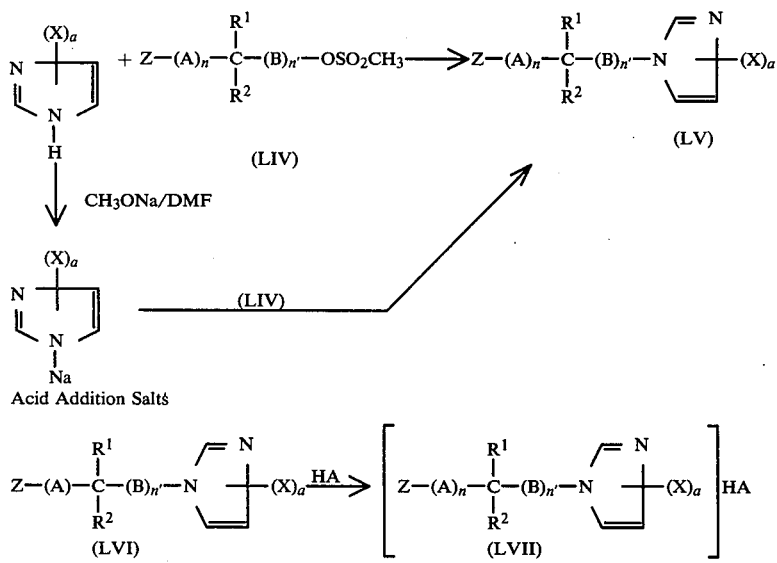

Acid Addition Salts

The salts of aralkyl imidazole derivatives are prepared by treating an ether solution of the imidazole (LVI) with an equivalent amount of the desired inorganic or organic acid dissolved in ether or alcohol followed by filtration or concentration then filtration to give the desired salt.

Metal Complex

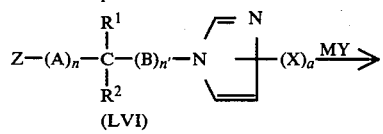

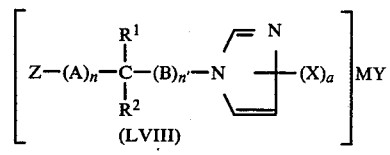

(LVIII)

The metal complex salts of the aralkyl imidazole derivatives (LVIII) are prepared by the treatment of an alcoholic or aqueous solution of the imidazole (LVI) with a metal salt at temperatures from about 15° C. to about 60° C.

The following examples are provided merely to illustrate the methods of preparation of the 1-substituted imidazoles and their metal complex salts. These examples are not to be considered in any ways as limitations of the scope of this invention.

EXAMPLE 1

1-[β-(2,4-dichlorophenyl) hexyl]imidazole 1. ethyl-β-(2,4-dichlorophenyl) hexanoate To 58.6 g (1.22 mole) of 50% sodium hydride in 1 liter of anhydrous tetrahydrofuran (THF) is added at 40°, 50.0 g (0.215 mole) of ethyl-2,4-dichlorophenyl acetate, and the mixture is stirred for 10 min. When the evolution of $H_2$ gas begins the temperature of the reaction is lowered to 10°, and 200.0 g (0.858 mole) of additional ester is added dropwise. When this addition is complete, the reaction is allowed to stir and to slowly warm up to ambient temperature. The reaction is then heated at 40° for 1 hour and then it is cooled to ambient temperature. To the mixture is added at 20°, 198.0 g (1.076 mole) of 1-iodobutane, and when this addition is complete, the reaction is stirred at 40° for 16 hours. The mixture is cooled, stripped down in volume, and poured into 1.5 liters of water. The insoluble oil is separated, and the aqueous layer is extracted with ether. The extract is combined with the oil. The ether solution is washed with 100 ml. of dilute hydrochloric acid, 100 ml. of sodium bicarbonate and finally 100 ml. of water. The solution is dried and concentrated to give 324.3 g. of crude product. Distillation of the product gives 223.0 g. (72%) of pure ester (115°-20°/0.25 mm). The material is identified by ir and its purity is determined by glc.

2. 2-(2,4-dichlorophenyl) hexan-1-ol

To 11.7 g. (0.308 mole) of lithium aluminum hydride in one liter of anhydrous ether at 5°-10° is slowly added 140.0 g. (0.486 mole) of the prepared ethyl-β-(2,4-dichlorophenyl) hexanoate. When the addition is complete, the reaction is allowed to stir and slowly warm to ambient temperature. The slurry is slowly added to iced water as $H_2$ gas vigorously evolves. When this addition is complete, the mixture is made acidic with concentrated hydrochloric acid. The organic layer which forms is separated, and the aqueous layer is extracted with ether. This extract is combined with the organic phase, and the solution is washed with water and then with dilute sodium bicarbonate solution. After drying over anhydrous magnesium sulfate, the ether solution is concentrated and distilled (118°-23°/0.2 mm) to give 110.8 g. (92%) of product.

3. 2-(2,4-dichlorophenyl) hexyl methane sulfonate

To 24.7 g. (0.1 mole) of the 2-(2,4-dichlorophenyl) hexan-2-ol and 13.8 g. (0.12 mole) of methane sulfonyl chloride in 200 ml. of benzene at 10° is slowly added 14.2 g. (0.14 mole) of triethylamine. When the addition is complete, the reaction is stirred, and allowed to come up to ambient temperature over a 30 minute period. The reaction slurry is then heated to reflux for 30 minutes, cooled and poured into water. The organic solution is washed with dilute hydrochloric acid then with water and finally with dilute sodium bicarbonate solution. After drying over anhydrous magnesium sulfate, the benzene is stripped off to yield 31.8 g. (98%) of the crude product. This material is identified by ir and nmr. The purity is determined by glc.

4. Imidazole Reaction

To 27.2 g. (0.4 mole) of imidazole at 95° is added 31.8 g (0.098 mole) of the 2-(2,4-dichlorophenyl) hexyl methane sulfonate, and the materials are stirred at 95° for 16 hours. At the end of this period the reaction is cooled, and poured into 500 ml. of water. After stirring for one hour the organic material is separate, and aqueous layer is extracted with ether. The ether is combined with the organic phase, and after a water wash is dried and concentrated to give 24.4 g. (88%) of product. The imidazole product is identified by ir, nmr, and elemental analysis. Its purity of greater than 95% is determine by glc.

EXAMPLE 2

1-[β-(2,4-dichlorophenyl) hexyl]-imidazole hydrochloride

In 30.0 g (0.101 mole) of 1-[β-(2,4-dichlorophenyl)-hexyl]imidazole dissolved in 200 ml of ether is bubbled dry hydrogen chloride gas until the mixture is acidic to litmus. A colorless solid forms which is separated by filtration to give 24.5 g. of the hydrochloride salt which is identified by nmr.

EXAMPLE 3

1-[β-(2,4-dichlorophenyl) hexyl]imidazole zinc chloride

Method A

To a solution of 2.0 g (0.0067 mole) of 1-[β-(2,4-dichlorophenyl)hexyl]imidazole in 10 ml of absolute ethanol is added dropwise a solution of 0.46 g (0.0036 mole) of zinc chloride in 30 ml of absolute ethanol. The reaction mixture is stirred at room temperature for 10 minutes and the solvent is removed under vacuum. A white glass-like solid is isolated as the product and is identified by nmr.

Method B

1-[β-(2,4-dichlorophenyl) hexyl]imidazole 2.0 g (0.0067 mole) and zinc chloride 0.92 g (0.0067 mole) are mixed in an acetone: methanol: water (1:1:2) solvent system, 40 ml. This preparation is immediately applied to plant foilage.

EXAMPLE 4

1-[β-2,4-dichlorophenyl) hexyl]imidazole oxalate

To a solution of 4 g (0.0135 mole) of 1-[β-(2,4-dichlorophenyl) hexyl]imidazole in ether is added dropwise a solution of 1.7 g (0.0135 mole) of oxalic acid dissolved in 10 ml of methanol. A white precipitate forms immediately. The precipitate is collected by filtration and dried under vacuum to give 3.37 g of a solid, m.p. 126°-128°.

EXAMPLE 26

1-[β-p-methylthiophenyl)hexyl]imidazole

1. p-Methylthiophenyl methanol

To 19.8 g (0.521 mole) of lithium aluminum hydride ($LiAlH_4$) in 750 ml of anhydrous ether is slowly added 98 g. (0.64 mole) of p-methyl mercaptobenzaldehyde in 250 ml of anhydrous ether at less than 10° C. When the addition is complete the reaction is stirred for 0.5 hour at 10° C. and then the reaction is stopped by slowly adding 100 ml of acetone to remove unreacted $LiAlH_4$.

To this mixture is added 500 ml of water and the reaction is made acidic by the addition of conc. hydrochloric acid. The ether layer is separated, dried over anhydrous magnesium sulfate, and concentrated to give 89.6 g of the crude product. This residue is crystallized from ether-hexane to give 75.8 g, mp 38°-40° (76% yield).

2. p-Methylthiophenyl acetonitrile

To 73.0 g (0.47 mole) of p-methylthiophenyl methanol and 59.6 g (0.52 mole) of methane sulfonyl chloride in 250 ml of benzene is slowly added 59.6 g (0.59 mole) of triethylamine over a period of one hour at less than 15° C. When the addition is complete, the reaction is stirred for one hour and allowed to warm up to ambient temperature.

The reaction mixture is combined with 400 ml of dilute hydrochloric acid. The benzene layer is separated, washed with 250 ml of $H_2O$, dried and concentrated to give 74.7 g of the crude mesylate product.

This residue is added to 25.5 g (0.52 mole) of sodium cyanide in 300 ml of dimethyl sulfoxide, and allowed to stir for one hour. The reaction is poured into iced water and the yellow tinted solid which forms is filtered and recrystallized from benzene-hexane to give 60.8 g (79%) of the product, mp 44°-5°.

3. 2-(p-Methylthiophenyl)hexanenitrile

To 12.5 g (0.25 mole) of 50% sodium hydride in 300 ml of anhydrous, distilled tetrahydrofurane is added 60.0 g (0.258 mole) of the p-methylthiophenyl acetonitrile over a period of one hour. The reaction mixture is allowed to stir for one hour then 48.8 g (0.265 mole) of 1-iodobutane is slowly added. When the addition is complete, the reaction is stirred for two hours. The mixture is combined with 500 ml of water and the organic phase is separated, washed with water and concentrated to give 80.1 g of crude product. Upon distillation 65.7 g (85%) of the product is isolated (126°-30°/0.01 mm.).

The imidazole derivative is then prepared by the method of Example 68 parts 2, 3, 4 and 5.

EXAMPLE 27

1-[β-(p-methylsulfonylphenyl)hexyl]imidazole

To 7.0 g (0.021 mole) of 1-[β-(p-methylthiophenyl)-hexyl]imidazole nitric acid salt in 75 ml of glacial acetic acid is added dropwise at less than 10°, 8.0 g (0.083 mole) of 35% hydrogen peroxide. When the addition is complete, the reaction is stirred for one hour heated on a steambath for a second hour and then poured into iced water. The solution is made basic to litmus with sodium hydroxide and the product is extracted out with ether.

The ether extract is treated with nitric acid and the salt settles out an oil. This material is treated with aqueous sodium hydroxide to give the product. An extraction with ether and concentration of that extraction gives 2.1 g (25%) of the methylsulfonyl product.

EXAMPLE 29

1-[β-(p-nitrophenyl)hexyl]imidazole

To a mixture of 20 ml of nitric acid and 10 ml of sulfuric acid at 5° is slowly added 10.0 g (0.044 mole) of 1-[β-phenylhexyl]imidazole in 10 ml of sulfuric acid. As soon as the addition is complete, the reaction is poured into iced water and the oil product settles out. The acidic solution is decanted and the remaining oil is washed with water, and then made basic with dilute sodium hydroxide. The product is extracted out with ether, dried and treated with nitric acid to precipitate the salt. The salt is recrystallized from acetoneether to give 4.8 g mp. 98°-100°. Treatment of the salt with dilute sodium hydroxide gives the free base product.

EXAMPLE 30

1-[β-(p-aminophenyl)hexyl]imidazole

To 5.0 g [0.0183 mole) of 1-[β-(p-nitrophenyl)hexyl]imidazole in 50 ml of methanol is added 2.0 g of conc. hydrochloric acid. The solution is heated to reflux and 4 one gram portions of iron filings are added at five min. intervals. When the additions are complete, the reaction slurry is stirred at reflux for 14 hours. The reaction is cooled, and then poured into water. The organic material is extracted out with toluene, dried and concentrated to give 4.5 g of the crude product.

The oil is dissolved in ether, and the solution is treated with nitric acid. The salt settles out as an oil. The oil is treated with dilute sodium hydroxide, extracted with ether, dried and concentrated to give 3.5 g of the imidazole product.

EXAMPLE 31

1-[β-(2,4-dichloro-5-nitrophenyl)hexyl]imidazole

To a solution of 40 ml of nitric acid and 10 ml of sulfuric acid, 14.8 g (0.0498 mole) of 1-[β-(2,4-dichlorophenyl)hexyl]imidazole in 30 ml of sulfuric acid is added at less than 5°. The reaction is stirred for ½ hour and then it is poured into acid water. The oily solid which separates is isolated by decanting off the dilute acid solution. The residue is washed and then treated with ammonium hydroxide solution.

The organic product is extracted out with ether, and the extract is dried and treated with dry hydrogen chloride. The hydrochloride salt precipitates out and is filtered to give 9.4 g of the crude product. A recrystallization of 2.7 g of this material from methanol gives 1.8 g of the purified hydrochloride salt, mp 99°-100°.

EXAMPLE 46

1-[β-(2,4-dimethylphenylphenyl)hexyl]imidazole 1. 2-(2,4-dimethylphenyl)hexan-1-ol To a stirred, 0° C. mixture of m-xylene 173 g (1.63 mole) and anhydrous stannic chloride 78.0 g (0.30 mole) which is constantly swept with nitrogen, is added dropwise, 1,2-epoxyhexane, 30.0 g (0.30 mole) in 50 g m-xylene. The exothermic temperature is maintained at 3° C. by the rate of addition. After the addition is completed, the reaction which now contains 223 g (2.0 mole) m-xylene is stirred for 30 minutes at 0° C. then poured into iced concentrated hydrochloric acid. The aqueous and organic layers are separated. After extracting the aqueous portion with ethyl ether, this organic layer is combined with the previous organic fraction. This combined organic material is washed successively with water, sodium bicarbonate and again water. The dried organic solvent mixture of ethyl ether and excess unreacted m-xylene is then removed on rotary evaporator. The concentrated residue is fractionally distilled in vacuo. The third fraction, 112° C./0.5 mm, is shown to be the desired product by spectral and analytical data. The yield is 35.6 g (57.6% theory).

2. 1-[β-(2,4-dimethylphenyl)hexyl]imidazole

The imidazole is formed from the alcohol by the method of Example 1 parts 3 and 4.

EXAMPLE 62

1-[α-(2,4-dimethoxyphenyl)hexyl]imidazole 1. 2-(2,4-dimethoxyphenyl)hexan-1-ol

To a stirred, 5° C. mixture of m-dimethoxybenzene 27.6 g (0.20 mole), anhydrous stannic chloride 52.1 g (0.20 mole) and 200 ml of methylene chloride which is constantly swept with nitrogen, is added dropwise, 1,2-epoxyhexane, 20.0 g (0.20 mole) in 50 ml of methylene chloride. The exothermic reaction temperature is maintained at 3° C. by the rate of addition. After the addition is complete, the reaction is stirred at 5° C. for 30 minutes, at which time it is poured into iced concentrated hydrochloric acid. The layers are separated and the aqueous layer is extracted with methylene chloride. The combined organic layers are washed with water followed by 5% sodium bicarbonate solution and finally water. The last water wash is neutral to pH paper. The methylene chloride solvent is removed on a rotary evaporator at 40° C. bath temperature. This residue is then fractionally distilled in vacuo. The third fraction, 140°-142° C./0.2 mm, is shown by nmr and ir to be the desired product. The yield is 25.32 g (55%, theory).

2. 1-[α-(2,4-dimethoxyphenyl)hexyl]imidazole

The above alcohol forms the methane sulfonate via the method of Example 1 part 3. However, upon reacting the methane sulfonate with imidazole by the method of Example 1 part 4, a rearrangement takes place and the α-substituted product is obtained which is identified by ir and nmr.

EXAMPLE 66

1-[α-(2,4-dichlorobenzyl)pentyl]imidazole

1. α-(2,4-dichlorobenzyl)pentan-1-ol

To 7.5 g (0.384 mole) of magnesium turnings in 150 ml of ether is added a 10.0 g (0.051 mole) portion of α,2,4-trichlorotoluene and a few crystals of iodine. When the iodine color has dissipated, the reaction is warmed to reflux, and 58.0 g (0.297 mole) of additional α,2,4-trichlorotoluene in 50 ml of ether is added at such a rate that the refluxing is maintained. When the addition is complete, the reaction is stirred at reflux for 2 hours and cooled. To this reaction mixture is added 17.0 g (0.197 mole) of valeraldehyde, and the reaction is heated again at reflux for 2 hours. The reaction is cooled and poured into ice cold dilute hydrochloric acid, and the organic phase is separated. The aqueous solution is extracted with ether, and the extract is combined with the organic phase. After a water wash, the organic solution is dried over anhydrous magnesium sulfate and stripped of solvent to give 57.2 g of crude product. A distillation provides 11.3 g (23%) of the product. Purity is determined by glc.

2. 1-(2,4-dichlorobenzyl)pentyl methane sulfonate

The methane sulfonate is prepared according to the method of Example 1 part 3, is identified by ir, and its purity determined by glc.

3. 1-[α-(2,4-dichlorobenzyl)pentyl]imidazole

The imidazole is prepared according to the method of Example 1 part 4, is identified by ir, nmr and elemental analysis and its purity of greater than 95% determined by glc.

EXAMPLE 67

1-[β-(2,4-dichlorobenzyl)hexyl]imidazole 1. ethyl α-(2,4-dichlorobenzyl)malonate To 4.6 g (0.095 mole) of 50% NaH in 250 ml of anhydrous THF is added with stirring 16.0 g (0.1 mole) of ethylmalonate, and the reaction slurry is allowed to stir for one hour, and then heated at reflux for three hours. The reaction is cooled, and to it is added 17.5 g (0.09 mole) α,2,4-trichlorotoluene. The resulting reaction slurry is heated to reflux for 16 hours. The reaction is cooled, and the THF is stripped off. The concentrate is stirred with water, and the ester product is extracted out with ether. The ether solution is washed with water, dried over anhydrous magnesium sulfate and concentrated to give the crude product. The residue is heated up to 110° under 0.1 mm pressure, and the excess ethyl malonate is distilled off leaving 27.1 g (94%) of the product. The purity of the material is greater than 95% by glc.

2. ethyl,α-butyl-α-(2,4-dichlorobenzyl) malonate

To 6.7 g (0.14 mole) of 50% sodium hydride in 500 ml of anhydrous THF is added at reflux, 44.2 g (0.139 mole) of the ethyl, α-(2,4-dichlorobenzyl) malonate, and the resulting slurry is stirred at reflux temperature for 16 hours. The reaction is cooled, and 26.6 g (0.14 mole) of 1-iodobutane is added. This mixture is heated, with stirring, at reflux for 6 hours.

The solvent is stripped off, and the concentrate is stirred with 500 ml of water. The product which separates is extracted out with ether and the ether is washed twice with 100 ml of water. After drying over anhydrous magnesium sulfate, the ether is stripped to yield 60 g (>100%) of the crude product. By glc this sample is 95% pure.

3. α-(2,4-dichlorobenzyl)hexanoic acid

To 45.0 g (0.40 mole) of 50% potassium hydroxide is added 52.4 g (0.14 mole) of the ethyl α-butyl-α-(2,4-dichlorobenzyl) malonate, and the mixture is stirred at reflux for 16 hours. The reaction is cooled, and washed twice with 75 ml of benzene. The aqueous solution is treated with concentrated hydrochloric acid, and the malonic acid derivative settles out. The oil is separated, and the aqueous solution is extracted with xylene. The extract is combined with the oil phase, dried over anhydrous magnesium sulfate and heated up to reflux. After two hours, the xylene is distilled off until the pot temperature reaches 180°. The reaction is cooled to give 46.0 g of crude product.

4. 2-(2,4-dichlorobenzyl) hexane-1-ol

To 9.4 g (0.248 mole) of lithium aluminum hydride in 600 ml of THF is slowly added, at less than 10°; 46.0 g of the crude α-(2,4-dichlorobenzyl) hexanoic acid. The reaction is allowed to stir, and slowly warm up to ambient temperature. After 2 hours, the slurry is heated to reflux and held there for 16 hours. At the end of this period, the reaction is cooled and carefully poured into ice water to decompose the excess LiAlH$_4$. The mixture is then made acidic by treatment with concentrated hydrochloric acid. The ether solution is separated, and the aqueous phase is extracted three times with 200 ml of ether. The extracts and the ether solution are combined and washed with 100 ml of dilute sodium bicarbonate solution and then with 100 ml of water. The solution is dried over anhydrous magnesium sulfate and the ether is stripped off to give 35.9 g of the crude alcohol product. Distillation (86.8°/0.15 mm) provides 34.2 g (93%) of pure alcohol. The material is identified by ir and its purity is determined by glc.

5. 2-(2,4-dichlorobenzyl) hexyl methane sulfonate

The methane sulfonate is prepared according to the method of Example 1 part 3, the product is identified by ir and its purity determined by glc.

6. 1-[β-(2,4-dichlorobenzyl) hexyl]imidazole

The imidazole is prepared according to the method of Example 1 part 4, the product is identified by ir, nmr and elemental analysis and its purity determined to be greater than 95% by glc.

EXAMPLE 68

1-[α-(2,4-dichlorophenyl) heptyl]imidazole

1. 2-(2,4-dichlorophenyl) hexyl cyanide

To a suspension of 11.3 g (0.23 mole) of sodium cyanide in 100 ml of dry dimethyl formamide (DMF) is added dropwise a solution of 50 g (0.154 mole) of 2-(2,4-dichlorophenyl)-hexylmethane sulfonate in 50 ml of DMF. The reaction mixture is stirred at 70° overnight. It is then poured into 500 ml of water and extracted with ether. The combined ether extracts are washed with water, then saturated saline solution and finally dried over magnesium sulfate. Solvent is evaporated under reduced pressure to give 37 g of crude product which is further purified by vacuum distillation (107.5°–110°/0.05 mm) to give 33.9 g (86%) of expected product.

2. 2-(2,4-dichlorophenyl) heptanoic acid

A mixture of 15 g (0.0596 mole) of 2-(2,4-dichlorophenyl) hexyl cyanide and 100 ml of 50% sulfuric acid is heated at 110° overnight. The reaction mixture is cooled and diluted with 500 ml of water. This aqueous portion is extracted with ether and the combined ether extracts are dried over magnesium sulfate. Solvent is removed under reduced pressure to give 15.02 g (93.7%) of a white solid, mp 65°–68°.

3. 3-(2,4-dichlorophenyl)-heptan-1-ol

To a suspension of 2.07 g (0.0545 mole) of lithium aluminum hydride in 100 ml of ether is added dropwise a solution of 15 g (0.054 mole) of 2-(2,4-dichlorophenyl) heptanoic acid in 50 ml of ether. The resulting mixture is stirred at room temperature for 3 hours. The excess lithium aluminum hydride is decomposed carefully with 100 ml of saturated ammonium chloride solution followed by 100 ml of dilute sulfuric acid solution. The ether layer is separated from the aqueous layer and the aqueous layer is again extracted with ether. The combined ether layers are washed with 10% sulfuric acid, water, saturated sodium bicarbonate solution, saturated saline solution and dried over magnesium sulfate. Solvent is evaporated under reduced pressure to give 12 g of an oil which is further purified by vacuum distillation (120°–125°/0.1 mm) to give 10.2 g (72%) of desired product.

4. 3-(2,4-dichlorophenyl)heptyl methane sulfonate

To 10.2 g (0.039 mole) of the 3-(2,4-dichlorophenyl) heptan-1-ol and 4.8 g (0.042 mole) of methane sulfonyl chloride in 100 ml of benzene at 10° is slowly added 4.4 g (0.043 mole) of triethylamine. When the addition is complete, the reaction is stirred and allowed to come up to ambient temperature over a 30 minute period. The reaction slurry is then heated to reflux for 30 minutes, cooled and poured into water. The organic solution is washed with dilute hydrochloric acid, then with water and finally with dilute sodium bicarbonate solution. After drying over anhydrous magnesium sulfate, the benzene is stripped off to give 10.6 g of crude sulfonate product.

5. 1-[δ-(2,4-dichlorophenyl) heptyl imidazole

To 10.6 g (0.160 mole) of imidazole at 95° is added 10.9 g (0.042 mole) of the crude 8-(2',4'-dichlorophenyl) heptyl methane sulfonate. The materials are stirred at 95° for 16 hours, cooled and poured into 500 ml of water. After stirring for 1 hr., the organic material is separated and the aqueous layer is extracted with ether. The ether is combined with the organic phase, and after a water wash, it is dried and concentrated to give 10.6 g of the crude product.

EXAMPLE 69

1-[β-(2,4-dichlorophenyl) phenethyl]imidazole

1. α-(2,4-dichlorophenyl) phenyl acetaldehyde

To 47.1 g (0.188 mole) of 2,4-dichlorobenzophenone and 36.2 g (0.289 mole) of ethyl chloroacetate is slowly added 14.9 g (0.31 mole) of 50% sodium hydride at 15°. The reaction is allowed to stir and slowly come up to ambient temperature overnight. The reaction is added to iced water, and made acidic with dilute hydrochloric acid. The organic material is extracted out with three 200 ml portions of benzene. The extracts are combined, washed twice with 100 ml of water and dried over anhydrous magnesium sulfate. The benzene is stripped off, and the crude product is added to 35.3 g (0.53 mole) of 85% potassium hydroxide in 350 ml of water. This mixture is refluxed for 20 hours, cooled and washed twice with 200 ml of benzene. The aqueous solution is acidified and the organic acid settles out as an oil. The oil is separated and the aqueous solution is extracted twice with 200 ml of ether. The extracts are combined with the oil, dried over anhydrous magnesium sulfate and concentrated to give 30.7 g of the hydroxy acid. This residue is heated for 3 hours at 140° to decompose it to the crude aldehyde product (24.3 g). Distillation (128°–137°/0.05 mm) gives 16.3 g (33%) of the aldehyde.

2. β-(2,4-dichlorophenyl) phenethanol

To 2.4 g (0.0615 mole) of LiAlH$_4$ in 140 ml of anhydrous THF is added dropwise, at 0°, 16.3 g (0.0615 mole) of the α-(2,4-dichlorophenyl) phenyl acetaldehyde in 60 ml of anhydrous THF. When the addition is complete, the reaction is stirred for 2 hours at 0° and then for 16 hours at ambient temperature. The reaction is then heated up to reflux for two hours, cooled and poured into ice water. The mixture is acidified with concentrated hydrochloric acid, and the organic material is extracted out twice with 200 ml portions of ether. The extracts are combined, dried over anhydrous magnesium sulfate and, concentrated to give 15.5 g of crude product. Distillation (125°–39°/0.025 mm) gives 10.6 g (65%) of the purified alcohol product. The material is identified by ir, and its purity is determined by glc.

3. β-(2,4-dichlorophenyl) phenethyl methane sulfonate

The methane sulfonate is prepared according to the method of Example 1 part 3, the product is identified by ir and its purity is determined by glc.

4. 1-[β-(2,4-dichlorophenyl) phenethyl]imidazole

The imidazole is prepared by the method of Example 1 part 4, the product is recrystallized from ether acetone to give 2.6 g (32%) of the hydrochloride salt, mp 197°–8°.

EXAMPLE 70

1-[ε-(2,4-dichlorophenyl) hexyl]imidazole

1. 5-(2,4-dichlorophenyl) hexan-1-ol

A slurry of m-dichlorobenzene, 735 g. (5.0 mole) and anhydrous aluminum chloride, 162 g. (1.1 mole) is cooled to 10° using an ice-water bath and 1,2-epoxyhexane, 100 g. (1.0 mole) is added dropwise over a one hour period. The temperature of the reaction is kept below 15°. The reaction mixture is allowed to come to room temperature and stirring is continued overnight. The reaction mixture is then poured into a 4 liter flask containing ice and concentrated hydrochloric acid (50 ml.) with stirring. The aqueous and organic layers are separated and the aqueous layer extracted three times with ether (150 ml). The combined organic extracts are washed twice with water (50 ml) and dried over magnesium sulfate. Solvent is evaporated and vacuum distillation (160°–172°/0.1 mm) gives 114 g. (46%) of product.

2. 1-[ε-(2,4-dichlorophenyl) hexyl]imidazole

The primary alcohol is converted into the sulfonate and imidazole compound in the usual manner.

EXAMPLE 71

1-[α-Methyl-β-(2,4-dichlorophenyl)hexyl]imidazole

1. 2,4-Dichlorovalerophenone

To 48.0 g. (0.398 mole) of valeryl chloride in 100.0 g. (0.680 mole) of m-dichlorobenzene is added portionwise at less than 5°, 66.7 g. (0.5 mole) of aluminum chloride. When the addition is complete, the reaction mixture is allowed to stir and slowly warm up to ambient temperature for 2 hours. It is then heated at reflux for 3 hours, and stirred at room temperature for 16 hours. The reaction mixture is poured into iced water, and made acidic with hydrochloric acid. The oil which formed separates, and the aqueous phase is extracted twice with 200 ml. of ether. The oil and the extracts are combined, washed with water, dried and concentrated to give 122.2 g. of the crude product. A distillation (89°–93°/0.05 mm) gives 55.2 g. (60%) of the product.

2. α-(2,4-dichlorophenyl) hexanal

To 50.0 g (0.216 mole) of 2,4-dichlorovalerophenone in 42.4 g (0.346 mole) of ethyl chloroacetate at 0° is added portionwise 8.7 g (0.363 mole) of sodium hydride over a 4 hour period. When the addition is complete, the reaction mixture is stirred and allowed to slowly warm up to ambient temperature for 2 hours. The reaction is then poured into iced water, and the mixture is made acidic with hydrochloric acid. The organic material is extracted out with ether, and the extract is dried and concentrated to give 89.2 of the crude glycidic ester. The residue is treated with 40.0 g (0.607 mole) of 85% potassium hydroxide in 400 ml of water, and the mixture is heated for 2 hours on a steambath. The alkaline solution is washed with benzene, and acidified with hydrochloric acid. The oil which forms is extracted out with ether, and the ether solution is dried and concentrated. The residue is dissolved in xylene, and heated at reflux for 6 hours with carbon dioxide evolution. The solution is stripped to dryness to give 32.4 g of the crude aldehyde. A distillation (112°–7°/0.2 mm) gave 16.6 g (31%) of the product.

3. 3-(2,4-dichlorophenyl) heptan-2-ol

To 14.3 g (0.088 mole) of methylmagnesium iodide in 75 ml of ether is slowly added at less than 10°, 14.5 g (0.059 mole) of the α-(2,4-dichlorophenyl) hexanal. When the addition is complete, the reaction is stirred for 1 hour then heated up to reflux for 2 hours. The reaction is cooled and poured into water. The mixture is acidified with hydrochloric acid and the oil which separates is extracted out with ether. The ether solution is dried and concentrated to give 11.7 g (76%) of the crude product.

4. 3-(2,4-dichlorophenyl) hept-2-ylmethane sulfonate

The methane sulfonate is prepared by the method of Example 1 part 3, the product is identified by ir and its purity determined by glc.

5. 1-[α-methyl-β-(2,4-dichlorophenyl)hexyl]imidazole

The imidazole is prepared according to the procedure of Example 1 part 4, the product is identified by ir and its purity determined by glc which shows it contains about equal amounts of isomeric products.

EXAMPLE 72

1-[β-butyl-β-(2,4-dichlorophenyl)hexyl]imidazole hydrochloride

1. ethyl, α-butyl-α-(2,4-dichlorophenyl) hexanoate

To 4.3 g (0.09 mole) of 50% sodium hydride in 200 ml of anhydrous tetrahydrofuran is added 23.6 g (0.0816 mole) of ethyl α-(2,4-dichlorophenyl) hexanoate, and the reaction is heated at reflux for 72 hours. The reaction is then stirred for 72 hours at ambient temperature. At the end of this period 16.6 g (0.09 mole) of iodobutane are added, and the reaction is heated at reflux for 24 hours. The reaction is cooled and poured into iced water, and the oil which forms is separated. The aqueous phase is extracted with ether, and the extract is combined with the oil. The ether solution is dried and concentrated to give 14.2 g of crude product. A distillation (150°–70°/0.25 mm) gives 13.3 g of the ester product.

2. 2-butyl-2-(2,4-dichlorophenyl) hexan-1-ol

The alcohol is formed by the method of Example 1 part 2, the pure product 4.8 g distills at 133°–8°/0.05 mm and is identified by nmr.

3. Imidazole Reaction

The imidazole is formed via the methane sulfonate according to the methods of Example 1 parts 3 and 4. The final product 1.5 g (28%) mp 103°–5° is recrystallized from acetone-ether and is identified by nmr and elemental analysis.

EXAMPLE 73

1-[β,β-bis (p-chlorophenyl) ethyl] imidazole

1. 2,2-bis (p-chlorophenyl) ethanol

To 15.1 g (0.397 mole) of lithium aluminum hydride in 750 ml of anhydrous tetrahydrofuran at less than 5° is added portionwise over a 2 hour period 95.0 g (0.338 mole) of bis (p-chlorophenyl) acetic acid. When the addition is complete, the reaction is stirred at 5° for 4 hours then allowed to warm up to ambient temperature overnight. The reaction is slowly poured into iced water with resulting evolution of hydrogen. The mixture is made acidic with hydrochloric acid, and the organic phase which forms is separated. The aqueous phase is extracted twice with 200 ml of ether and the extracts are combined with the organic phase. The ether solution is dried and concentrated to give 74.9 g of crude product. This residue is distilled (157°–62°/0.05 mm) to give 35.3 g (39%) of the product.

2. Formation of Imidazole

The imidazole derivative (m.p. 80°–2°) is formed by the usual route.

EXAMPLE 74

1-[β-(o&p-chlorophenyl)p-chlorophenethyl] imidazole

1. 2-(o&p-chlorophenyl)-p-chlorophenethyl chloride

To a mixture of 12.5 ml of 30% oleum in 25 ml of sulfuric acid is added dropwise at less than 35°, 11.6 g (0.76 mole) of chloroacetaldehyde diethyl acetal in 34.0 g (0.30 mole) of chlorobenzene. When the addition is complete, the reaction is stirred for 1 hour, and warmed up to ambient temperature. The reaction mixture is poured into iced water, and the organic phase is extracted out twice with 200 ml of ether. The extracts are dried and concentrated to give 17.3 g of the yellow-orange crude product. The material is distilled to give 9.8 g (165°–8°/0.4 mm) of the isomeric product.

2. Reaction with Imidazole

To 75 ml of methanol is added 1.05 g (0.0458 mole) of sodium to form a solution. To this solution is then added 3.1 g (0.0458 mole) of imidazole, and the reaction is stripped to dryness. To the wet solid residue is added 50 ml of N,N-dimethylformamide. The resulting solution is heated up to 130°, and the remaining methanol is distilled off. To this dimethylformamide solution is added 8.7 g (0.0305 mole) of the 2-(o&p-chlorophenyl)-p-chlorophenethyl chloride, and the reaction is heated up to 130° for 48 hours. The reaction is cooled, poured into iced water and the organic material is extracted out with ether. The ether extract is cooled and treated with hydrogen chloride gas. The oil salt which formed is separated, and treated with a sodium bicarbonate solution. The resulting mixture is extracted with ether and the ether solution is dried and concentrated to give 0.6 g of the product.

Example 75

1-[β,β-tetramethylene-β-(2,4-dichlorophenyl)ethyl-]imidazolium nitrate

1. α,α-tetramethylene-2,4-dichlorobenzyl cyanide

Into a 500 ml three-necked flask is placed 200 ml of 25% sodium hydroxide solution and 4 g of tetraethyl ammonium bromide. To this suspension is added dropwise a solution of 33.5 g (0.2 mole) of 2,4-dichlorobenzyl cyanide and 43 g (0.2 mole) of 1,4-dibromobutane in 200 ml of methylene chloride under nitrogen. When the addition is over, the reaction mixture is heated to reflux for 1.5 hours. It is then poured into water and the layers are separated. The aqueous layer is extracted with 100 ml of methylene chloride. The combined organic extracts are washed with water, saturated sodium chloride solution and dried over magnesium sulfate. Solvent is evaporated to give a light yellow oil. Vacuum distillation (130°–140°/0.2 mm) gives 30.4 g (63%) of pure product, which is identified by nmr.

2. α,α-tetramethylene-2,4-dichlorophenyl acetic acid

A mixture of 14 g (0.06 mole) of α,α-tetramethylene-2,4-dichlorobenzyl cyanide, 160 ml of 40% potassium hydroxide solution, and 120 ml of diethylene glycol is heated under reflux for 3 days. The reaction mixture is poured into water and extracted with ether. The aqueous layer is then made acidic with hydrochloric acid followed by extraction with ether. The combined ether extracts from the acidic solution are washed with water, saturated sodium chloride solution and then dried over magnesium sulfate. Solvent is evaporated to give 12.4 g of crude acid which is recrystallized from hexane-benzene to give 8 g of pure acid, m.p. 136°–138°.

3. 2,2-tetramethylene-2-(2,4-dichlorophenyl)-ethyl alcohol

To a suspension of 3 g (0.08 mole) of lithium aluminum hydride in 300 ml of anhydrous ether is added dropwise 13 g (0.05 mole) of α,α-tetramethylene-2,4-dichlorophenyl acetic acid in 50 ml of ether under nitrogen. The reaction mixture is then heated to reflux for one hour. Excess lithium aluminum hydride is carefully decomposed by dropwise addition of 10% hydrochloric acid into the reaction mixture. The two layers are separated and the aqueous layer is extracted with ether. The combined ether extracts are washed with water and dried over magnesium sulfate. Solvent is evaporated to give 9.8 g of alcohol, which is identified by nmr.

4. 2,2-tetramethylene-2-(2,4-dichlorophenyl)ethyl methane sulfonate

To a mixture of 9.8 g (0.04 mole) of 2,2-tetramethylene-2-(2,4-dichlorophenyl) ethyl alcohol and 5 g (0.04 mole) of methane sulfonyl chloride in 30 ml of benzene is added dropwise 5 g (0.05 mole) of triethyl amine. The reaction mixture is stirred at room temperature overnight. The precipitate formed is filtered. The benzene solution is washed with water then dilute hydrochloric acid and dried over magnesium sulfate. Solvent is evaporated to give 12 g of product, which is identified by nmr.

5. 1-[β,β-tetramethylene-β-(2,4-dichlorophenyl)ethyl]imidazole

A mixture of 12 g (0.037 mole) of 2,2-tetramethylene-2-(2,4-dichlorophenyl)ethyl methane sulfonate, 10 g (0.15 mole) of imidazole, and 1 ml of dimethyl formamide is heated at 140° for 24 hours. The reaction mixture is poured into water and extracted with ether. The combined ether extracts are washed with water and dried over magnesium sulfate. The drying agent is filtered and to the ethereal solution is added conc. nitric acid dropwise. The white precipitate which forms is collected by filtration and dried under vacuo. A total of 3.7 g of the salt is obtained m.p. 176°–179°, which is identified by nmr.

EXAMPLE 101

1-[β-(2,4-dichlorophenyl)hexyl]-4-nitroimidazole

To 1.3 g (0.0307 mole) of sodium hydroxide in 150 ml of methanol is added 3.5 g (0.0307 mole) of 4-nitroimidazole, and the solution is heated and the methanol distilled off. To the concentrate is added 100 ml of dimethyl formamide and the solution is heated up to 120° to remove the excess methanol and water. This dimethyl formamide solution is then cooled to less than 90° and 10.0 g (of 0.0307 mole) of 2-(2,4-dichlorophenyl)hexyl methane sulfonate is added. The reaction mixture is heated up to 145° for two hours and then cooled and poured into water. The organic material is extracted out with ether and after drying, the extract is stripped to give 11.2 g of residue. The concentrate is triturated with hexane and then dissolved in 25 ml of methanol. The methanol solution is poured slowly into water and a gummy solid forms. This solid is separated by filtration, dried and recrystallized from acetone-hexane to give 4.2 g (41%) of the product, m.p. 67°–9°.

EXAMPLE 102

1-[β-(2,4-dichlorophenyl)hexyl]4,5-dichloroimidazole

To 100 ml of methanol is added 1.7 g (0.0735 moles) of sodium. When the sodium dissolves, 10 g (0.0735 moles) of 4,5-dichlorimidazole is added. The mixture is stirred until a solution forms, and then the methanol is stripped off. The wet residue is then added to 50 ml of dimethyl formamide and the solution heated up to 125° to remove the remaining methanol and water. The solution is cooled to less than 100° and 2.5 g (0.0735 moles)

of 2-(2,4-dichlorophenyl)hexyl methane sulfonate is added. The reaction is heated up to 130° for two hours and then cooled. The reaction is poured into water and the organic material extracted three times with 200 ml of benzene. The combined extracts are washed twice with 50 ml of water, dried over anhydrous magnesium sulfate and concentrated to obtain 15.8 g of the crude product. The residue is dissolved in ether, and treated with dry hydrogen chloride gas. The ether solution is decanted from the oil which forms and the oil is triturated twice with 150 ml of ether. The oil is then treated with 10% sodium hydroxide, and the product extracted out twice with 200 ml of ether. The ether solution is dried and concentrated to give 12.6 g (47%) of the oil product.

EXAMPLE 103

1-[β-(2,4-dichlorophenyl)hexyl]-3-butylimidazolium iodide

1-[β-(2,4-dichlorophenyl)hexyl]imidazole 5.0 g (0.0168 moles) is heated for two hours on a steambath with 3.1 g (0.0168 moles) of 1-iodobutane. The reaction is cooled and triturated three times with 50 ml of ether. The oil residue is stripped to dryness to give 5.3 g (66%) of the oil product.

EXAMPLE 104

1-[β-(2,4-dichloro-5-nitrophenyl)hexyl] nitroimidazole

To 1-[β-(2,4-dichlorophenyl)hexyl]imidazole 20.0 g (0.067 mole) in 40 ml of sulfuric acid is slowly added 80 ml of nitric acid and 40 ml of sulfuric acid. The reaction is heated on a steambath for 14 hours, cooled and poured into water. The aqueous acidic solution is decanted from the oil which forms. The residue is washed twice with 75 ml of water, and then taken up in acetone-benzene, dried and concentrated to give 14.9 g of the crude product. To purify, 3.0 g of the crude product is dissolved in hot methanol. Upon cooling the product precipitates out is separated by filtration and dried to give 1.6 g of the nitro imidazole derivative.

The following Tables I and II present some of the compounds prepared by procedures presented in the preceding examples. These tables are presented as a further illustration of the types of compounds encompossed by the present invention and are not to be construed in anyway as limitations of the scope of this invention.

TABLE I

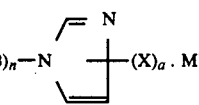

| Example No. | Z | $(A)_n$ | $R^1$ | $R^2$ | $(B)_{n'}$ | $(X)_a$ | MY |
|---|---|---|---|---|---|---|---|
| 1 | 2,4-$Cl_2C_6H_3$ | — | $C_4H_9n$ | H | $CH_2$ | — | — |
| 2 | 2,4-$Cl_2C_6H_3$ | — | $C_4H_9n$ | H | $CH_2$ | — | HCl |
| 3 | 2,4-$Cl_2C_6H_3$ | — | $C_4H_9n$ | H | $CH_2$ | — | ½ $ZnCl_2$ |
| 4 | 2,4-$Cl_2C_6H_3$ | — | $C_4H_9n$ | H | $CH_2$ | — | $C_2H_2O_4$ |
| 5 | 2,4-$Cl_2C_6H_3$ | — | $C_4H_9n$ | H | $CH_2$ | — | ½ $CuBr_2$ |
| 6 | 2,4-$Cl_2C_6H_3$ | — | $C_4H_9n$ | H | $CH_2$ | — | ½ $CuSO_4$ |
| 7 | 2,4-$Cl_2C_6H_3$ | — | $C_4H_9n$ | H | $CH_2$ | — | ½ $CoCl_2$ |
| 8 | 2,4-$Cl_2C_6H_3$ | — | $C_4H_9n$ | H | $CH_2$ | — | ½ $NiSO_4$ |
| 9 | 2,4-$Cl_2C_6H_3$ | — | $C_4H_9n$ | H | $CH_2$ | — | ½ $FeCl_2$ |

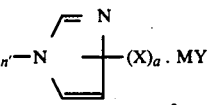

| Example No. | Z | $(A)_n$ | $R^1$ | $R^2$ | $(B)_{n'}$ | $(X)_a$ | MY |
|---|---|---|---|---|---|---|---|
| 10 | 2,4-$Cl_2C_6H_3$ | — | $C_4H_9n$ | H | $CH_2$ | — | ⅓ $Cr(NO_3)_3$ |
| 11 | 2,6-$Cl_2C_6H_3$ | — | $C_4H_9n$ | H | $CH_2$ | — | HCl |
| 12 | 2-$CH_3C_6H_4$ | — | $C_4H_9n$ | H | $CH_2$ | — | — |
| 13 | 3-$CH_3C_6H_4$ | — | $C_4H_9n$ | H | $CH_2$ | — | — |
| 14 | 4-$CH_3C_6H_4$ | — | $C_4H_9n$ | H | $CH_2$ | — | HCl |
| 15 | 4-$CH_3O$—$C_6H_4$ | — | $C_4H_9n$ | H | $CH_2$ | — | — |
| 16 | $C_6H_5$ | — | $C_4H_9n$ | H | $CH_2$ | — | — |
| 17 | 4-$ClC_6H_4$ | — | $C_4H_9n$ | H | $CH_2$ | — | HCl |
| 18 | 4-$ClC_6H_4$ | — | $C_4H_9n$ | H | $CH_2$ | — | — |
| 19 | 3-$ClC_6H_4$ | — | $C_4H_9n$ | H | $CH_2$ | — | — |
| 20 | 2-$ClC_6H_4$ | — | $C_4H_9n$ | H | $CH_2$ | — | HCl |

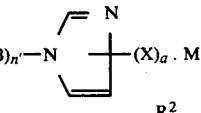

| Example No. | Z | $(A)_n$ | $R^1$ | $R^2$ | $(B)_{n'}$ | $(X)_a$ | MY |
|---|---|---|---|---|---|---|---|
| 21 | 3,4-$Cl_2C_6H_3$ | — | $C_4H_9n$ | H | $CH_2$ | — | — |
| 22 | 2,4-$(CH_3)_2C_6H_3$ | — | $C_4H_9n$ | H | $CH_2$ | — | — |
| 23 | 3-$CF_3C_6H_4$ | — | $C_4H_9n$ | H | $CH_2$ | — | — |
| 24 | 4-$FC_6H_4$ | — | $C_4H_9n$ | H | $CH_2$ | — | — |
| 25 | 4-$BrC_6H_4$ | — | $C_4H_9n$ | H | $CH_2$ | — | HCl |
| 26 | 4-$CH_3SC_6H_4$ | — | $C_4H_9n$ | H | $CH_2$ | — | $HNO_3$ |
| 27 | 4-$CH_3SO_2C_6H_4$ | — | $C_4H_9n$ | H | $CH_2$ | — | — |
| 28 | 4(t-$C_4H_9$)$C_6H_4$ | — | $C_4H_9n$ | H | $CH_2$ | — | — |
| 29 | 4-$NO_2C_6H_4$ | — | $C_4H_9n$ | H | $CH_2$ | — | — |
| 30 | 4-$NH_2C_6H_4$ | — | $C_4H_9n$ | H | $CH_2$ | — | — |
| 31 | 2,4-$Cl_2$-5-$NO_2C_6H_2$ | — | $C_4H_9n$ | H | $CH_2$ | — | HCl |
| 32 | 2,6-$(CH_3)_2C_6H_3$ | — | $C_4H_9n$ | H | $CH_2$ | — | HCl |

TABLE I-continued

| | | | | | | | |
|---|---|---|---|---|---|---|---|
| 33 | 3,5-(CH$_3$)$_2$C$_6$H$_3$ | — | C$_4$H$_9$n | H | CH$_2$ | — | — |
| 34 | C$_6$H$_5$-C$_6$H$_5$ | — | C$_4$H$_9$n | H | CH$_2$ | — | — |
| 35 |  | — | C$_4$H$_9$n | H | CH | — | — |
| 36 |  | — | C$_4$H$_9$n | H | CH$_2$ | — | 2 . HNO$_3$ |
| 37 | 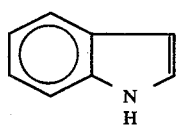 | — | C$_4$H$_9$n | H | CH$_2$ | — | C$_2$H$_2$O$_4$ |
| 38 | 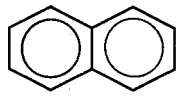 | — | C$_4$H$_9$n | H | CH$_2$ | — | — |
| 39 | 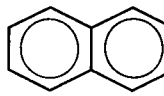 | — | C$_4$H$_9$n | H | CH$_2$ | — | — |
| 40 | 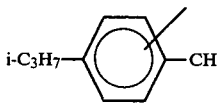 | — | C$_4$H$_9$n | H | CH$_2$ | — | — |
| 41 | 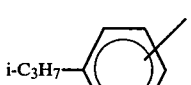 | — | C$_4$H$_9$n | H | CH$_2$ | — | — |
| 42 | 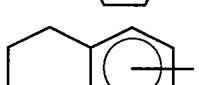 | — | C$_4$H$_9$n | H | CH$_2$ | — | — |
| 43 | 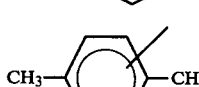 | — | C$_4$H$_9$n | H | CH$_2$ | — | — |
| 44 | 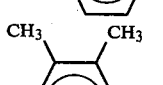 | — | C$_4$H$_9$n | H | CH$_2$ | — | — |
| 45 |  | — | C$_4$H$_9$n | H | CH$_2$ | — | — |
| 46 |  | — | C$_4$H$_9$n | H | CH$_2$ | — | — |
| 47 | 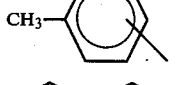 | — | C$_4$H$_9$n | H | CH$_2$ | — | — |
| 48 |  | — | C$_4$H$_9$n | H | CH$_2$ | — | — |
| 49 | 2,4-Cl$_2$C$_6$H$_3$ | — | —CH$_2$CH=CH$_2$ | H | CH$_2$ | — | HNO$_3$ |
| 50 | 2,4-Cl$_2$C$_6$H$_3$ | — | 4-ClC$_6$H$_4$CH$_2$— | H | CH$_2$ | — | — |
| 51 | 2,4-Cl$_2$C$_6$H$_3$ | — | —(CH$_2$)$_2$C$_6$H$_4$F-4 | H | CH$_2$ | — | HCl |

TABLE I-continued

| # | Col2 | Col3 | Col4 | Col5 | Col6 | Col7 |
|---|------|------|------|------|------|------|
| 52 | 2,4-Cl$_2$C$_6$H$_3$ | — | C$_6$H$_{11}$ | H | CH$_2$ | 2H$_2$O · HCl |
| 53 | 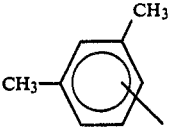 2,4,6-trimethylphenyl | — | CH$_3$ | H | CH$_2$ | — |
| 54 | 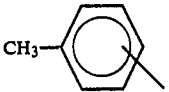 2,6-dimethylphenyl | — | CH$_3$ | H | CH$_2$ | — |
| 55 | 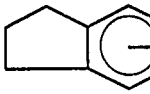 indanyl | — | C$_2$H$_5$ | H | CH$_2$ | HNO$_3$ |
| 56 | 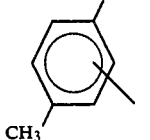 2,5-dimethylphenyl | — | C$_2$H$_5$ | H | CH$_2$ | — |
| 57 | 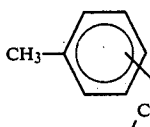 2,6-dimethylphenyl | — | C$_2$H$_5$ | H | CH$_2$ | — |
| 58 | 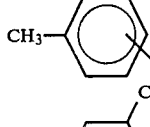 2,3-dimethylphenyl | — | C$_2$H$_5$ | H | CH$_2$ | — |
| 59 | 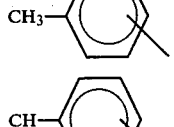 2,3-dimethylphenyl | — | C$_6$H$_{13}$n | H | CH$_2$ | — |
| 60 | 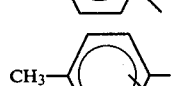 | — | C$_6$H$_{13}$n | H | CH$_2$ | — |
| 61 | 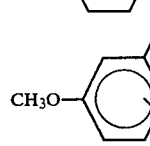 2,6-dimethylphenyl | — | C$_6$H$_{13}$n | H | CH$_2$ | — |
| 62 | 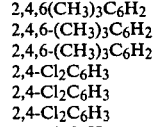 2,6-dimethoxyphenyl | CH$_2$ | C$_4$H$_9$n | H | — | — |
| 63 | 2,4,6(CH$_3$)$_3$C$_6$H$_2$ | CH$_2$ | C$_6$H$_{13}$n | H | — | — |
| 64 | 2,4,6-(CH$_3$)$_3$C$_6$H$_2$ | CH$_2$ | C$_2$H$_5$ | H | — | — |
| 65 | 2,4,6-(CH$_3$)$_3$C$_6$H$_2$ | CH$_2$ | C$_4$H$_9$n | H | — | — |
| 66 | 2,4-Cl$_2$C$_6$H$_3$ | CH$_2$ | C$_4$H$_9$n | H | — | — |
| 67 | 2,4-Cl$_2$C$_6$H$_3$ | CH$_2$ | C$_4$H$_9$n | H | CH$_2$ | — |
| 68 | 2,4-Cl$_2$C$_6$H$_3$ | — | C$_4$H$_9$n | H | (CH$_2$)$_2$ | — |
| 69 | 2,4-Cl$_2$C$_6$H$_3$ | — | C$_6$H$_5$ | H | CH$_2$ | HCl |
| 70 | 2,4-Cl$_2$C$_6$H$_3$ | — | CH$_3$ | H | (CH$_2$)$_4$ | — |
| 71 | 2,4-Cl$_2$C$_6$H$_3$ | — | C$_4$H$_9$n | H | CHCH$_3$ | — |
| 72 | 2,4-Cl$_2$C$_6$H$_3$ | — | C$_4$H$_9$n | C$_4$H$_9$n | CH$_2$ | HCl |
| 73 | 4-ClC$_6$H$_4$ | — | 4-ClC$_6$H$_4$ | H | CH$_2$ | — |
| 74 | 4-ClC$_6$H$_4$ | — | Cl | H | CH$_2$ | — |
| 75 | 2,4-Cl$_2$C$_6$H$_3$ | — | CH$_2$CH$_2$CH$_2$CH$_2$— | | CH$_2$ | HNO$_3$ |
| 76 | 4-CH$_3$C$_6$H$_4$ | — | 4-CH$_3$C$_6$H$_4$ | H | CH$_2$ | HCl |
| 77 | 4-BrC$_6$H$_4$ | — | C$_4$H$_9$n | H | CH$_2$ | — |
| 78 | 4-ClC$_6$H$_4$ | — | 4-ClC$_6$H$_4$ | H | CH$_2$ | HCl |
| 79 | 4-ClC$_6$H$_4$ | — | 2-ClC$_6$H$_4$ | H | CH$_2$ | — |
| 80 | 2,4-Cl$_2$C$_6$H$_3$ | (CH$_2$)$_2$ | C$_4$H$_9$n | H | CH$_2$ | HCl |

TABLE I-continued

| | | | | | | | |
|---|---|---|---|---|---|---|---|
| 81 | 2,4-$Cl_2C_6H_3$ | — | H | H | $CH_2$ | — | $HNO_3$ |
| 82 | 2,4-$Cl_2C_6H_3$ | — | $CH_3$ | H | $CH_2$ | — | HCl |
| 83 | 2,4-$Cl_2C_6H_3$ | — | $CH_3$ | H | $CH_2$ | — | — |
| 84 | 2,4-$Cl_2C_6H_3$ | — | $C_2H_5$ | H | $CH_2$ | — | — |
| 85 | 2,4-$Cl_2C_6H_3$ | — | $C_6H_{13}n$ | H | $CH_2$ | — | — |
| 86 | 2,4-$Cl_2C_6H_3$ | — | $C_8H_{17}n$ | H | $CH_2$ | — | — |
| 87 | 2,4-$Cl_2C_6H_3$ | — | $C_{10}H_{21}n$ | H | $CH_2$ | — | — |
| 88 | 2,4-$Cl_2C_6H_3$ | — | —$CH_2CH(CH_3)_2$ | H | $CH_2$ | — | — |
| 89 | 2,4-$Cl_2C_6H_3$ | — | $C_6H_5CH_2$— | H | $CH_2$ | — | — |
| 90 | 2,4-$Cl_2C_6H_3$ | — | $C_6H_5(CH_2)_2$— | H | $CH_2$ | — | — |
| 91 | 2,4-$Cl_2C_6H_3$ | — | $C_6H_9$ | H | $CH_2$ | — | HCl |
| 92 | $C_6H_5$ | — | $C_6H_5$ | H | $CH_2$ | — | HCl |
| 93 | 4-Cl-$C_6H_4$ | — | $C_6H_5$ | H | $CH_2$ | — | — |
| 94 | 2,4-$Cl_2C_6H_3$ | $CH_2$ | $CH_3$ | H | — | — | — |
| 95 | $C_6H_5$ | $CH_2$ | $C_4H_9n$ | H | — | — | — |
| 96 | $C_6H_5$ | $CH_2$ | $CH_3$ | H | — | — | — |
| 97 | $C_6H_5$ | — | $CH_3$ | $CH_3$ | $CH_2$ | — | HCl |
| 98 | 2 or 4-$ClC_6H_4$ | — | $CH_3$ | H | $(CH_2)_2$ | — | — |
| 99 | 4Cl-$C_6H_4$ | — | $CH_3$ | $CH_3$ | $CH_2$ | — | HCl |
| 100 | 2,4-$Cl_2C_6H_3$ | — | $C_4H_9n$ | H | $CH_2$ | 2-$CH_3$ | — |
| 101 | 2,4-$Cl_2C_6H_3$ | — | $C_4H_9n$ | H | $CH_2$ | 4-$NO_2$ | $H_2O$ |
| 102 | 2,4-$Cl_2C_6H_3$ | — | $C_4H_9n$ | H | $CH_2$ | 4,5-$Cl_2$ | — |
| 103 | 2,4-$Cl_2C_6H_3$ | — | $C_4H_9n$ | H | $CH_2$ | 3-$C_4H_9n$ | HI |
| 104 | 2,4-$Cl_2$—5-$NO_2C_6H_2$ | — | $C_4H_9n$ | H | $CH_2$ | —$NO_2$ | — |

TABLE II

| Example Number | mp. | C | H | Cl | N | O | Other |
|---|---|---|---|---|---|---|---|
| 1 | conc. | 60.64 (60.62) | 6.16 (6.10) | 24.01 (23.86) | 9.16 (9.42) | | |
| 2 | 139–41 | 51.48 (53.99) | 5.60 (5.74) | 30.30 (31.87) | 7.89 (8.40) | | |
| 3 | 57–63 | 48.75 (49.31) | 4.94 (4.97) | 29.70 (29.11) | 6.88 (7.67) | | 7.58 Zn = (8.95) |
| 4 | 126–8 | 54.22 (52.73) | 5.33 (5.21) | 19.20 (18.31) | 7.56 (7.23) | 14.16 (16.53) | |
| 5 | 219–21 | 38.00 (44.06) | 3.92 (4.44) | 16.26 (17.34) | 5.87 (6.85) | | 13.00 Cu = (7.77) |
| 6 | 61–4 | 52.35 (47.79) | 5.38 (4.81) | 21.08 (18.81) | 7.51 (7.43) | 5.49 (8.49) | 4.70 Cu = (8.43) |
| 7 | 53–8 | 49.68 (49.75) | 5.16 (5.01) | 7.10 (7.73) | 28.45 (29.37) | | 7.60 Co = (8.14) |
| 8 | 107–113 | 45.75 (48.05) | 4.87 (4.84) | 18.96 (15.23) | 6.91 (7.47) | 10.54 (8.53) | 5.23 Ni = (4.23) |
| 9 | 45.50 | 49.77 (49.96) | 5.13 (5.03) | 30.12 (29.49) | 6.92 (7.77) | | 5.70 Fe = (7.74) |
| 10 | 44–9 | 40.67 (43.28) | 4.81 (4.36) | 16.78 (17.03) | 10.14 (11.78) | 18.97 (17.29) | 3.2 Cr = (6.24) |
| 11 | 154–6 | 53.63 (53.99) | 5.74 (5.74) | 31.79 (31.87) | 8.26 (8.39) | | |
| 12 | conc. | 77.93 (79.29) | 9.21 (9.15) | — | 11.32 (11.56) | | |
| 13 | conc. | 78.36 (79.29) | 9.11 (9.15) | — | 11.75 (11.56) | | |
| 14 | 126–8 | 68.65 (68.92) | 8.47 (8.32) | 12.21 (12.71) | 9.75 (10.05) | | |
| 15 | conc. | 72.99 (74.40) | 8.42 (8.58) | — | 11.20 (10.84) | 7.35 (6.17) | |
| 16 | conc. | 77.36 (78.90) | 8.70 (8.83) | — | 11.87 (12.27) | | |
| 17 | 72–3 | 56.82 (60.21) | 6.26 (6.74) | 22.24 (23.70) | 8.91 (9.36) | | |
| 18 | conc. | 66.80 (68.56) | 7.25 (7.29) | 14.72 (13.49) | 9.52 (10.66) | | |
| 19 | conc. | 66.08 (68.56) | 7.19 (7.29) | 12.78 (13.49) | 10.25 (10.66) | | |
| 20 | 103–6 | 56.76 (60.21) | 6.32 (6.74) | 22.09 (23.70) | 8.23 (9.36) | | |
| 21 | conc. | 60.25 (60.61) | 6.27 (6.10) | 24.91 (23.85) | 8.30 (9.42) | | |
| 22 | conc. | 78.06 (79.64) | 9.46 (9.44) | — | 10.83 (10.93) | | |
| 23 | conc. | 63.31 (64.85) | 6.34 (6.46) | — | 10.84 (9.45) | | 18.62 F = (19.23) |
| 24 | conc. | 72.06 (73.14) | 8.05 (7.77) | — | 10.20 (11.37) | | 7.96 F = (7.71) |
| 25 | conc. | 51.62 (52.42) | 6.00 (5.87) | 9.15 10.32 | 7.62 (8.15) | | 22.76 Br = (23.25) |
| 26 | 108–10 | 56.48 (56.95) | 6.81 (6.87) | — | 13.06 (12.45) | 13.89 (14.22) | 9.32 S = 9.50 |

TABLE II-continued

| Example Number | mp. | C | H | Cl | N | O | Other |
|---|---|---|---|---|---|---|---|
| 27 | conc. | 62.06 (62.71) | 7.48 (7.24) | — | 8.57 (9.14) | 10.86 (10.44) | 9.62 S = (10.47) |
| 28 | conc. | 79.96 (80.23) | 10.06 (9.92) | — | 9.75 (9.85) | | |
| 29 | conc. | 65.40 (65.91) | 7.19 (7.01) | — | 15.42 (15.37) | 12.58 11.71 | |
| 30 | conc. | 73.64 (74.03) | 8.92 (8.70) | | 16.84 (17.27) | | |
| 31 | 99–100 | 45.37 (45.41) | 5.11 (5.06) | 26.73 (26.81) | 10.55 (10.59) | 11.72 (12.09) | |
| 32 | conc. | 78.23 (79.64) | 9.85 (9.44) | — | 10.77 (10.93) | | |
| 33 | conc. | 78.97 (79.64) | 9.79 (9.44) | — | 10.54 (10.93) | | |
| 34 | conc. | 79.73 (82.85) | 7.71 (7.95) | — | 8.75 (9.20) | | |
| 35 | conc. | 66.46 (66.62) | 7.79 (7.74) | — | 11.70 (11.95) | | 13.42 S = (13.68) |
| 36 | 103–5 | 47.38 (47.32) | 6.06 (5.96) | — | 19.96 (19.71) | 26.24 (27.01) | |
| 37 | 128–30 | 61.90 (62.27) | 6.49 (6.60) | — | 11.88 (11.46) | 20.59 (21.83) | |
| 38 | conc. | 81.47 (82.00) | 8.17 (7.95) | — | 9.41 (10.05) | | |
| 39 | conc. | 78.95 (82.00) | 7.80 (7.95) | — | 9.25 (10.05) | | |
| 40 | conc. | 78.20 (80.23) | 9.99 (9.92) | — | 9.34 (9.85) | | |
| 41 | conc. | 74.50 (79.94) | 9.51 (9.69) | — | 9.67 (10.36) | | |
| 42 | conc. | 79.63 (80.55) | 9.48 (9.01) | — | 9.87 (10.44) | | |
| 43 | conc. | 76.36 (79.64) | 9.50 (9.44) | — | 10.32 (10.93) | | |
| 44 | conc. | 76.82 (79.64) | 9.46 (9.44) | — | 10.13 (10.93) | | |
| 45 | conc. | 77.50 (78.28) | 9.30 (9.15) | — | 10.46 (11.56) | | |
| 46 | conc. | 78.81 (79.64) | 9.73 (9.44) | — | 10.36 (10.93) | | |
| 47 | conc. | 78.30 (82.00) | 8.49 (7.95) | — | 9.19 (10.05) | | |
| 48 | conc. | 81.12 (82.85) | 8.21 (7.95) | — | 9.68 (9.20) | | |
| 49 | 108–10 | 48.87 (48.85) | 4.44 (4.39) | 20.94 (20.60) | 11.92 (12.21) | 13.44 (13.95) | |
| 50 | conc. | 58.68 (59.12) | 4.54 (4.13) | 28.86 (29.09) | 7.44 (7.66) | | |
| 51 | 152–3 | 57.04 (57.08) | 4.58 (4.54) | 26.60 (26.61) | 7.17 (7.01) | | 4.50 F = (4.75) |
| 52 | conc. | 52.05 (51.55) | 5.62 (5.85) | 26.82 (26.85) | 7.78 (7.07) | | |
| 53 | conc. | 74.45 (78.46) | 8.90 (8.46) | — | 11.92 (13.09) | | |
| 54 | conc. | 76.82 (77.96) | 8.23 (8.05) | — | 13.75 (13.99) | | |
| 55 | 111–2 | 62.28 (63.35) | 7.16 (6.98) | — | 13.87 (13.85) | | |
| 56 | conc. | 78.48 (78.90) | 9.18 (8.83) | — | 11.56 (12.27) | | |
| 57 | conc. | 77.14 (78.46) | 8.54 (8.46) | — | 12.96 (13.09) | | |
| 58 | conc. | 77.71 (78.90) | 8.94 (8.83) | — | 11.74 (12.27) | | |
| 59 | conc. | 79.35 (80.23) | 10.03 (9.92) | — | 9.14 (9.85) | | |
| 60 | conc. | 79.47 (79.94) | 9.70 (9.69) | — | 9.27 (10.36) | | |
| 61 | conc. | 78.29 (80.23) | 9.88 (9.92) | — | 8.85 (9.85) | | |
| 62 | conc. | 70.60 (70.80) | 8.10 (8.39) | — | 9.90 (9.72) | | |
| 63 | conc. | 78.80 (80.48) | 10.21 (10.13) | — | 8.93 (9.39) | | |
| 64 | conc. | 76.70 (79.28) | 9.29 (9.15) | — | 10.94 (11.56) | | |
| 65 | conc. | 79.75 (79.94) | 9.96 (9.69) | — | 10.20 (10.36) | | |
| 66 | conc. | 59.93 (60.61) | 6.14 (6.10) | 22.52 (23.86) | 9.10 (9.43) | | |

TABLE II-continued

| Example Number | mp. | C | H | Cl | N | O | Other |
|---|---|---|---|---|---|---|---|
| | | 61.31 | 6.86 | 23.28 | 8.62 | | |
| 67 | conc. | (61.74) | (6.48) | (22.78) | (9.00) | | |
| | | 60.46 | 6.21 | 23.99 | 8.13 | | |
| 68 | conc. | (61.74) | (6.48) | (22.78) | (9.00) | | |
| | | 58.82 | 4.38 | 28.44 | 8.04 | | |
| 69 | 197–8 | (57.73) | (4.28) | (30.07) | (7.92) | | |
| | | 60.39 | 6.46 | 23.50 | 8.94 | | |
| 70 | conc. | (60.62) | (6.10) | (23.86) | (9.42) | | |
| | | 61.33 | 6.42 | 23.10 | 8.34 | | |
| 71 | conc. | (61.74) | (6.48) | (22.78) | (9.00) | | |
| | | 54.93 | 6.54 | 25.44 | 6.70 | | |
| 72 | 103–5 | (58.55) | (6.98) | (27.29) | (7.19) | | |
| | | 64.59 | 4.44 | 21.81 | 8.65 | | |
| 73 | 80–2 | (64.37) | (4.45) | (22.35) | (8.83) | | |
| 74 | conc. | | | | | | |
| | | 49.78 | 4.78 | 20.07 | 11.60 | 13.86 | |
| 75 | 176–9 | (50.29) | (4.78) | (19.79) | (11.79) | (13.40) | |
| | | 69.42 | 6.81 | 11.15 | 8.75 | | |
| 76 | 195–7 | (72.92) | (6.77) | (11.33) | (8.96) | | |
| | | 57.40 | 6.01 | — | 8.25 | | Br = 28.58 |
| 77 | conc. | (58.64) | (6.23) | | (9.12) | | (26.01) |
| | | 58.00 | 4.11 | 29.89 | 7.69 | | |
| 78 | 248–50 | (57.73) | (4.28) | (30.07) | (7.92) | | |
| | | 63.38 | 4.60 | 22.11 | 8.03 | | |
| 79 | conc. | (64.30) | (4.41) | (22.40) | (8.85) | | |
| | | 56.50 | 6.54 | 28.83 | 7.97 | | |
| 80 | 137–8 | (56.44) | (6.41) | (29.40) | (7.75) | | |
| | | 43.13 | 3.74 | 22.98 | 13.99 | | |
| 81 | 109–11 | (43.42) | (3.61) | (23.35) | (13.81) | | |
| | | 49.20 | 4.54 | 36.07 | 9.60 | | |
| 82 | 163–6 | (49.42) | (4.49) | (36.47) | (9.61) | | |
| | | 56.68 | 4.88 | 27.37 | 11.11 | | |
| 83 | conc. | (56.49) | (4.74) | (27.79) | (10.98) | | |
| | | 56.95 | 5.33 | 26.26 | 10.02 | | |
| 84 | conc. | (58.01) | (5.24) | (26.34) | (10.41) | | |
| | | 61.92 | 6.84 | 22.27 | 8.57 | | |
| 85 | conc. | (62.77) | (6.82) | (21.80) | (8.61) | | |
| | | 63.16 | 7.23 | 19.54 | 7.17 | | |
| 86 | conc. | (64.59) | (7.42) | (20.07) | (7.93) | | |
| | | 65.32 | 8.05 | 18.35 | 5.84 | | |
| 87 | conc. | (66.00) | (7.86) | (18.65) | (7.35) | | |
| | | 57.92 | 6.36 | 23.16 | 9.25 | | |
| 88 | conc. | (60.60) | (6.07) | (23.90) | (9.43) | | |
| | | 64.42 | 5.01 | 21.85 | 8.13 | | |
| 89 | conc. | (65.27) | (4.87) | (21.41) | (8.46) | | |
| | | 64.31 | 5.31 | 20.75 | 7.71 | | |
| 90 | conc. | (66.19) | (5.25) | (20.54) | (8.11) | | |
| | | 54.33 | 5.39 | 28.91 | 7.38 | | |
| 91 | 175–7 | (57.08) | (5.35) | (29.73) | (7.83) | | |
| | | 62.62 | 6.38 | 11.98 | 8.88 | | |
| 92 | 83–5 | (71.70) | (6.02) | (12.45) | (8.94) | | |
| | | 71.38 | 5.41 | 12.81 | 9.90 | | |
| 93 | conc. | (72.21) | (5.35) | (12.54) | (9.91) | | |
| | | 55.59 | 4.96 | 27.14 | 11.30 | | |
| 94 | conc. | (56.49) | (4.74) | (27.79) | (10.98) | | |
| | | 76.62 | 8.67 | | 12.52 | | |
| 95 | conc. | (78.90) | (8.83) | — | (12.27) | | |
| | | 76.58 | 7.57 | | 15.08 | | |
| 96 | conc. | (77.38) | (7.58) | — | (15.04) | | |
| | | 58.92 | 6.64 | 15.61 | 12.56 | | |
| 97 | 165 dec. | (65.95) | (7.24) | (14.98) | (11.83) | | |
| | | 65.70 | 6.74 | 15.09 | 11.58 | | |
| 98 | conc. | (66.52) | (6.44) | (15.10) | (11.93) | | |
| | | 53.56 | 6.15 | 25.16 | 11.13 | | |
| 99 | 168–75 | (57.58) | (5.95) | (26.15) | (10.33) | | |
| | | 58.73 | 6.70 | 23.79 | 7.86 | | |
| 100 | conc. | (61.74) | (6.47) | (22.78) | (9.00) | | |
| | | 50.65 | 4.90 | 19.39 | 11.63 | 13.54 | |
| 101 | 67–9 | (50.05) | (5.23) | (19.70) | (11.67) | (13.33) | |
| | | 50.55 | 4.83 | 38.62 | 6.59 | | |
| 102 | conc. | (49.21) | (4.40) | (38.74) | (7.65) | | |
| | | 47.67 | 5.98 | 15.39 | 5.87 | | 24.39 |
| 103 | conc. | (47.42) | (5.66) | (14.73) | (5.82) | | I = (26.37) |
| | | 46.60 | 4.20 | 18.34 | 14.37 | 17.00 | |
| 104 | conc. | (46.53) | (4.17) | (18.31) | (14.47) | (16.53) | |

The metal salt complexes of the above 1-substituted aralkyl imidazoles can be prepared by adding dropwise, with stirring, a stoichiometric amount of a metal salt dissolved in an appropriate solvent to a solution of the 1-substituted aralkyl imidazole dissolved in a similarly appropriate solvent. The reaction mixture is briefly stirred and the solvent is removed under reduced pressure to give the metal salt complex of the respective 1-substituted aralkyl imidazole. Identification and purity are determined by elemental analysis.

The metal salt complexes can also be prepared by mixing stoichiometric or excess amounts of the metal salt and 1-substituted aralkyl imidazole in the desired amount of solvent containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications.

Solvents that can be utilized in these procedures include any polar solvent, e.g., water, methanol, ethanol, isopropanol or ethylene glycol and any aprotic dipolar solvent e.g., dimethylsulfoxide, acetonitrile, dimethylformamide, nitromethane or acetone.

The metal salt cations that may be used in these procedures can be selected from the group consisting of calcium, magnesium, manganese, copper, nickel, zinc, iron, cobalt, tin, cadmium, mercury, chromium, lead and barium and the like.

Any appropriate anion e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

It has also been found that any metal containing fungicides can also act as safening agents when used in place of metal salts. Typical metal containing fungicides that can be utilized in these procedures are: (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); (b) copper-based fungicides such as: cuprous oxide, copper naphthenate, and Bordeaux mixture; and (c) miscellaneous fungicides such as: phenylmercuric acetate N-ethylmercuri-1,2,3,6-tetrahydro-3,6-endomethano-3,4,5,6,7,7-hexachlorophthalimide, phenylmercuri monoethanolammonium lactate, nickel-containing compounds and calcium cyanamide.

The compounds and metal salt complexes of this invention are excellent as systemic protectant/eradicant fungicides and possess a high degree of activity against assorted phytopathogenic fungi. Certain compounds are particularly effective for the control of grey mold of faba beans (*Botyrytis cinerea*), rice blast (*Piricularia oryzae*) on rice plants, tomato late blight (*Phytophtora infestans*) on tomato seedlings, bean powdery mildew (*Erysiphe polygoni*) on bean plants, barley net blotch (*Helminthosporium teres*) on barley plants, grape downy mildew (*Plasmopora viticola*) on grape seedlings, citrus decay (*Penicillium digitatum*) on citrus fruit, apple scab (*Venturia inaequalis*) on apple seedlings, wheat powdery mildew (*Erysiphe graminis*) on wheat plants, wheat black point (*Alternaria tenius*) on wheat plants, black rot of grapes (*Guignardia bidwellii*) on grape seedlings, cucumber powdery mildew (*Erysiphe cichoracearum*) on cucumber plants, and the organism responsible for the production of aflatoxin (*Aspergillus flavus*).

The compounds eradicant fungicidal properties are unique in that they kill *Helminthosporium teres* in infected plant tissues a property not possessed by current fungicides used to control diseases incited by Helminthosporium spp. The systemic properties possessed by these compounds are equally unique in their ability to move both acropetally and basipetally in plant tissues.

As the free base these compounds can be used to control seedborne *Helminthosporium oryzae* a property which is found in no other fungicides other than the organic mercury compounds.

These compounds as the free base possess growth regulatory activity in both dicotyledonous and monocotyledonous plants, the most pronounced effect being a retardation of plant growth. In some cases, particularly in dicotyledonous plants, some of the growth regulatory properties may be considered adverse. When this occurs, the growth regulatory and phytotoxic plant responses may be suppressed by metal salt complexation of the imidazole compounds with elements selected from Groups IIA, IVA, VA, IB, IIB, VIB, VIIB and VIII of the Periodic Table.

In evaluating these compounds, a preliminary fungicidal evaluation is carried out using the compounds at 300 ppm and spraying the plants to run off in a carrier volume of about 150 gallons/acre.

The general procedure is to take potted plants in proper condition of growth for susceptibility to the fungal disease to be evaluated to spray these on a moving belt and allow to dry. The proper plants are then inoculated with the fungal spores and then allowed to incubate until the disease has developed and the control read or estimated. The percent disease control is reported by the following rating system:

A = 97–100% control
B = 90–96% control
C = 70–89% control
D = 50–69% control
E = Inactive < 50% control % disease control = disease of untreated-disease of treated × 100 disease of untreated The phytopathogenic fungi used in the evaluation of the fungicidal activity of the compounds and salts of this invention are described below.

BH—barley net blotch (*Helminthosporium teres*)
BOT—grey mold of faba beans (*Botyrytis cinerea*)
BPM—bean powdery mildew (*Erysiphe polygoni*)
GDM—grape downy mildew (*Plasmopora viticola*)
TLB—tomato late blight (*Phytophtora infestans*)
RB—rice blast (*Piricularia oryzae*)
WSR—wheat stem rust (*Puccinia graminis* f. sp. *tritici*)
WLR—wheat leaf rust (*Puccinia recondita*)

Table III presents the results of the application of some of the compounds and salts of this invention at a rate of 300 ppm evaluated against the above fungi.

TABLE III

| Example No. | BH | BOT | BPM | GDM | TLB | RB | WSR | WLR |
|---|---|---|---|---|---|---|---|---|
| 1 | A | B | A | B | E | B | — | A |
| 2 | A | B | A | A | B | A | — | A |
| 3 | A | A | A | A | B | B | — | A |
| 4 | E | B | A | A | A | B | — | A |
| 5 | A | C | A | A | B | E | — | A |
| 6 | A | A | A | B | B | E | — | A |
| 7 | A | A | A | A | A | A | — | A |
| 8 | A | A | A | A | B | B | — | A |
| 9 | A | A | A | A | A | A | — | A |
| 10 | A | A | A | A | B | A | — | A |
| 11 | E | E | A | B | B | B | — | A |
| 12 | A | E | A | E | B | A | — | A |

TABLE III-continued

| Example No. | BH | BOT | BPM | GDM | TLB | RB | WSR | WLR |
|---|---|---|---|---|---|---|---|---|
| 13 | E | E | A | — | E | E | — | E |
| 14 | A | E | A | B | A | — | — | E |
| 15 | A | E | A | B | E | B | — | C |
| 16 | A | E | E | E | C | A | — | C |
| 17 | A | E | A | B | A | E | — | B |
| 18 | A | E | A | A | A | E | — | A |
| 19 | E | E | A | B | B | B | — | A |
| 20 | A | E | A | B | A | E | — | A |
| 21 | A | B | A | B | B | B | — | A |
| 22 | A | E | A | A | A | B | — | A |
| 23 | E | E | E | E | E | — | E | — |
| 24 | A | C | A | C | E | — | C | — |
| 25 | A | C | A | E | E | — | E | — |
| 26 | E | C | A | E | E | — | E | — |
| 27 | — | E | E | E | — | — | E | — |
| 28 | — | E | A | E | B | — | B | — |
| 29 | A | C | A | C | E | — | C | — |
| 30 | E | E | B | C | E | A | A | — |
| 31 | E | C | A | E | E | — | E | — |
| 32 | B | A | A | E | E | — | C | — |
| 33 | E | C | A | C | B | — | E | — |
| 34 | E | C | A | C | E | — | B | — |
| 35 | A | E | A | C | E | — | E | — |
| 36 | E | E | A | E | E | — | E | — |
| 37 |   |   |   |   |   |   |   |   |
| 38 | A | E | A | B | A | — | B | — |
| 39 |   |   |   |   |   |   |   |   |
| 40 | A | E | A | E | E | — | E | — |
| 41 | E | C | A | E | — | — | E | — |
| 42 | E | E | A | C | A | — | C | — |
| 43 | E | C | A | C | E | — | E | — |
| 44 | E | E | A | B | A | — | E | — |
| 45 | E | E | A | E | E | A | E | — |
| 46 | A | E | A | A | E | — | C | — |
| 47 | A | C | E | E | E | — | C | — |
| 48 | A | C | A | A | E | A | A | — |
| 49 | E | B | E | C | E | — | B | — |
| 50 | A | B | A | B | E | — | A | — |
| 51 | B | A | A | B | B | — | B | — |
| 52 | A | A | A | B | E | A | A | — |
| 53 | E | E | A | E | E | E | C | — |
| 54 | E | E | A | E | E | — | E | — |
| 55 | E | E | A | E | E | — | E | — |
| 56 | A | E | A | E | E | — | E | — |
| 57 | E | C | A | E | E | — | E | — |
| 58 | A | A | E | E | E | C | E | — |
| 59 | A | E | A | E | E | B | B | — |
| 60 | E | E | A | E | E | B | E | — |
| 61 | E | C | A | E | E | — | E | — |
| 62 | A | C | A | E | C | — | C | — |
| 63 | E | B | E | C | — | — | C | — |
| 64 | A | E | A | E | E | — | C | — |
| 65 | A | E | A | E | A | B | E | — |
| 66 | B | C | A | A | A | A | — | C |
| 67 | A | D | A | A | B | A | — | A |
| 68 | A | E | B | A | B | E | — | C |
| 69 | A | A | A | B | A | A | — | A |
| 70 | A | E | E | B | B | B | — | E |
| 71 | A | E | A | A | B | A | — | A |
| 72 | E | B | A | E | E | B | — | A |
| 73 | A | B | B | E | B | B | — | A |
| 74 | A | A | A | A | A | E | — | A |
| 75 | A | A | A | A | A | A | — | B |
| 76 | E | E | A | B | B | B | — | E |
| 77 | E | E | A | C | E | — | E | — |
| 78 | A | A | A | E | B | B | — | A |
| 79 | E | B | A | B | — | B | — | A |
| 80 | A | E | A | B | C | B | — | A |
| 81 | E | E | A | E | E | E | — | E |
| 82 | A | C | A | A | C | E | — | E |
| 83 | A | C | A | B | B | E | — | B |
| 84 | A | E | A | E | E | E | — | B |
| 85 | E | C | A | E | E | A | — | A |
| 86 | A | C | A | E | E | B | — | A |
| 87 | A | C | E | E | E | B | — | A |
| 88 | E | E | A | E | E | B | — | A |
| 89 | E | C | A | B | B | B | — | A |
| 90 | E | B | A | B | B | B | — | A |
| 91 | A | B | A | B | B | B | — | A |
| 92 | E | E | A | E | B | B | — | E |
| 93 | A | E | A | E | B | B | — | A |
| 94 | A | E | A | E | E | — | — | A |
| 95 | E | E | A | E | E | — | — | A |
| 96 | E | E | E | E | E | E | — | E |
| 97 | E | E | E | E | E | B | — | E |
| 98 | E | E | E | E | E | B | — | E |
| 99 | A | E | A | E | — | E | — | A |
| 100 | E | E | E | E | B | B | — | E |
| 101 | E | E | A | C | E | A | A | — |
| 102 | E | E | A | C | E | A | A | — |
| 103 | E | A | A | B | B | — | E | — |
| 104 | E | E | B | B | E | A | A | — |

The aralkylimidazoles and their metal salt complexes of this invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these aralkylimidazoles or their metal salt complexes can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc., publication "Detergents and Emulsifiers Annual."

In general, the compounds of this invention can be dissolved in certain solvents such as acetone, methanol, ethanol, dimethylformamide, pyridine or dimethyl sulfoxide and such solutions extended with water. The concentration of the solution can vary from 1% to 90% with a preferred range being 5 to 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of 1-[β-(2,4-dichlorophenyl)hexyl]imidazole, 45 parts of a synthetic precipitated hydrated silicon dioxide sold under the trademark Hi-Sil ®, and 5 parts of sodium lignosulfonate (Marasperse ® N-22). In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ® 7.

Dusts are prepared by mixing the aralkylimidazole or its metal salt complex with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

The aralkylimidazoles or their metal salt complex can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually about 0.1 lb. to 50 lbs. per acre of the active ingredient.

As a seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre. As a foliar fungicide, the toxicant is usually applied to growing plants at a rate of 0.25 to 10 lbs. per acre.

Fungicides which can be combined with the fungicides of this invention includes:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), and 3,5-dimethyl-1,3,5-2H-tetrahydrothiadiazine-2-thione (dazomet);

(b) nitrophenol derivatives such as:
dinitro-(1-methylheptyl) phenyl crotonate (dinocap),
2-sec-butyl-4,6-dinitrophenyl 3,3-dimethyl acrylate (binapacryl), and
2-sec-butyl-4,6-dinitrophenyl isopropyl carbonate;

(c) heterocyclic structures such as:
N-trichloromethylthiotetrahydro-phthalimide (captan),
N-trichloromethylthiopthalimide (folpet),
2-heptadecyl-2-imidazoline acetate (glyodin),
2-octylisothiazolone-3,
2,4-dichloro-6-(o-chloroanilino)-s-triazine,
diethyl phthalimidophosphorothioate,
4-butyl-1,2,4-triazole,
5-amino-1-[bis(dimethylamino)phosphinyl]-3-phenyl-1,2,4-triazole,
5-ethoxy-3-trichloromethyl-1,2,4-thiadizole,
2,3-dicyano-1,4-dithiaanthraquinone (dithianon),
2,thio-1,3-dithio-[4,5-b]quinoxaline (thioquinox),
methyl 1-(butylcarbamoyl)-2-benzimidazole carbamate (benomyl),
2-(4-thiazolyl) benzimidazole (thiabendazole),
4-(2-chlorophenylhydrazono)-3-methyl-5-isoxazolone,
pyridine-2-thiol-1-oxide,
8-hydroxyquinoline sulfate,
2,3-dihydro-5-carboxanilido-6-methyl-1,4-oxathiin-4,4-dioxide,
2,3-dihydro-5-carboxanilido-6-methyl-1,4-oxathiin,
α-(phenyl)-α-(2,4-dichlorophenyl)-5-pyrimidinylmethanol (triarimol),
cis-N-[(1,1,2,2-tetrachloroethyl)thio]-4-cyclohexene-1,2-dicarboximide,
3-[2-(3,5-dimethyl-2-oxycyclohexyl)-2-hydroxyl]-glutarimide (cycloheximide),
dehydroacetic acid,
N-(1,1,2,2-tetrachloroethylthio)-3a,4, 7,7a-tetrahydrophthalimide (captafol),
5-butyl-2-ethylamino-4-hydroxy-6-methylpyrimidine (ethirimol),
acetate of 4-cyclododecyl-2,6-dimethylmorpholine (dodemorph), and
6-methyl-2-oxo-1,3-dithiolo[4,5-b]-quinoxaline (quinomethionate).

(d) miscellaneous halogenated fungicides such as:
tetrachloro-p-benzoquinone (chloranil),
2,3-dichloro-1,4-naphthoquinone (dichlone),
1,4-dichloro-2,5-dimethoxybenzene (chloroneb),
3,5,6-trichloro-o-anisic acid (tricamba),
2,4,5,6-tetrachloroisophthalonitrile (TCPN),
2,6-dichloro-4-nitroaniline (dicloran),
2-chloro-1-nitropropane,
polychloronitrobenzenes such as:
pentachloronitrobenzene (PCNB) and
tetrafluorodichloroacetone;

(e) fungicidal antibiotics such as:
griseofulvin,
kasugamycin and
streptomycin;

(f) copper-based fungicides such as:
cuprous oxide,
basic cupric chloride,
basic copper carbonate,
copper naphthenate, and
Bordeaux mixture; and (g) miscellaneous fungicides such as:
diphenyl,
dodecylguanidine acetate (dodine),
phenylmercuric acetate,
N-ethylmercuri-1,2,3,6-tetrahydro-3,6-endomethano-3,4,5,6,7,7,-hexachlorophthalimide,
phenylmercuric monoethanol ammonium lactate,
p-dimethylaminobenzenediazo sodium sulfonate,
methyl isothiocyanate,
1-thiocyano-2,4-dinitrobenzene,
1-phenylthiosemicarbazide,
nickel-containing compounds,
calcium cyanamide,
lime sulfur,
sulfur, and
1,2-bis(3-methoxycarbonyl-2-thioureido)benzene (thiophanate-methyl).

The compounds and metal salt complexes of this invention can be advantageously employed in various ways. Since the metal salt complexes possess inherent systemicity and broad spectrum fungicidal activity, they can be employed in the storage of cereal grain. These complexes can also be employed as fungicides in turf and fruit orchard applications. Other applications of the metal salt complexes of this invention will suggest themselves to those skilled in the art of agriculture and horticulture.

We claim:

1. A chemical compound selected from the group consisting of an imidazole derivative having the formula

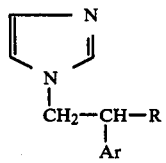

and the active acid addition salts thereof wherein Ar is a member selected from the group consisting of phenyl, mono-, di- and trihalophenyl, methylphenyl, ethylphenyl, methoxyphenyl, ethoxyphenyl, nitrophenyl and trihalomethylphenyl, and R is a member selected from the group consisting of ($C_1$-$C_{10}$) alkyl, cycloalkyl, alkenyl, cycloalkenyl and aralkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl, provided that when Ar is unsubstituted phenyl then R is ($C_4$-$C_{10}$) alkyl, cycloalkyl, alkenyl, cycloalkenyl and arylalkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl, 2. A chemical compound selected from the group consisting of an imidazole derivative having the formula

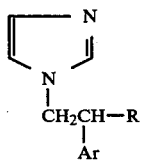

and the active acid addition salts thereof wherein Ar is a member selected from the group consisting of phenyl, mono-, di- and trihalophenyl, methylphenyl, ethylphenyl, methoxyphenyl, ethoxyphenyl, nitrophenyl and trihalomethylphenyl, and R is a member selected from the group consisting of alkenyl, cycloalkenyl and aralkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl.

3. A chemical compound selected from the group consisting of an imidazole having the formula

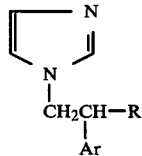

and the active acid addition salts thereof wherein Ar is a member selected from the group consisting of phenyl, mono-, di- and trihalophenyl, methylphenyl, ethylphenyl, methoxyphenyl, ethoxyphenyl, nitrophenyl and trihalomethylphenyl, and R is a member selected from the group consisting of ($C_1$-$C_{10}$) alkyl and cycloalkyl provided that when Ar is unsubstituted phenyl then R is ($C_4$-$C_{10}$) alkyl or cycloalkyl.

4. A chemical compound selected from the group consisting of 1-[2-(2,4-dichlorophenyl)hexyl]-1H-imidazole and the active acid addition salts thereof.

5. A chemical compound selected from the group consisting of 1-[2-(2,4-dichlorophenyl)decyl]-1H-imidazole and the active acid addition salts thereof.

6. A chemical compound selected from the group consisting of 1-[2-(2,4-dichlorophenyl)-4-methylpentyl]-1H-imidazole and the active acid addition salts thereof.

7. A chemical compound selected from the group consisting of an imidazole derivative having the formula

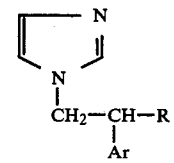

and the active acid addition salts thereof wherein Ar is a member selected from the group consisting of phenyl, mono-, di- and trihalophenyl, methylphenyl, ethylphenyl, methoxyphenyl, ethoxyphenyl, nitrophenyl and trihalomethylphenyl, and R is a member selected from the group consisting of ($C_1$-$C_{10}$) alkyl, ($C_3$-$C_7$) cycloalkyl, ($C_2$-$C_{12}$) alkenyl, ($C_5$-$C_7$) cycloalkenyl and ($C_7$-$C_9$) arylalkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl.

8. A chemical compound according to claim 7 wherein R is ($C_4$-$C_{10}$) alkyl, ($C_3$-$C_7$) cycloalkyl, ($C_2$-$C_{12}$) alkenyl, ($C_5$-$C_7$) cycloalkenyl and ($C_7$-$C_9$) arylalkyl, said aryl being a member selected from the group consisting of phenyl, mono-, di-, and trihalophenyl, methylphenyl, ethylphenyl, methoxyphenyl, ethoxyphenyl, nitrophenyl and trihalomethylphenyl when Ar is unsubstituted phenyl.

9. A chemical compound according to claim 7 wherein R is a member selected from the group consisting of ($C_1$-$C_{10}$) alkyl and ($C_3$-$C_7$) cycloalkyl provided that when Ar is unsubstituted phenyl then R is ($C_4$-$C_{10}$) alkyl or ($C_3$-$C_7$) cycloalkyl.

10. A method for controlling phytopathogenic fungi which comprises applying to a plant, to plant seeds or to the plant habitat an effective amount of a compound of the formula:

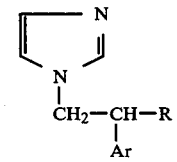

and the active acid addition salts thereof wherein Ar is a member selected from the group consisting of phenyl, mono-, di- and trihalophenyl, methylphenyl, ethylphenyl, methoxyphenyl, ethoxyphenyl, nitrophenyl and trihalomethylphenyl, and R is a member selected from the group consisting of ($C_1$-$C_{10}$) alkyl, ($C_3$-$C_7$) cycloalkyl, ($C_2$-$C_{12}$) alkenyl, ($C_5$-$C_7$) cycloalkenyl and ($C_7$-$C_9$) aralkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl.

11. A method according to claim 10 wherein the compound is applied to the plant or plant habitat at a rate of 0.1 to 50 lbs. per acre.

12. A method according to claim 10 wherein the compound is applied to the plant seeds at a rate of 0.1 to 20 ounces per hundred pounds of seed.

13. A fungicidal composition for controlling phytopathogenic fungi which comprises an agronomically acceptable carrier and, as the active ingredient, a compound of the formula:

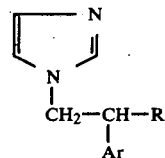

and the active acid addition salts thereof wherein Ar is a member selected from the group consisting of phenyl, mono-, di- and trihalophenyl, methylphenyl, ethylphenyl, methoxyphenyl, ethoxyphenyl, nitrophenyl and trihalomethylphenyl, and R is a member selected from the group consisting of $(C_1-C_{10})$ alkyl, $(C_3-C_7)$ cycloalkyl, $(C_2-C_{12})$ alkenyl, $(C_5-C_7)$ cycloalkenyl and $(C_7-C_9)$ aralkyl, said aryl being a member selected from the group consisting of phenyl, mono-, di- and trihalophenyl, methylphenyl, ethylphenyl, methoxyphenyl, ethoxyphenyl, nitrophenyl and trihalomethylphenyl.

* * * * *